(12) United States Patent
Carrey et al.

(10) Patent No.: US 8,416,291 B2
(45) Date of Patent: Apr. 9, 2013

(54) SYSTEM TO AID IN THE POSITIONING, CONFIRMATION AND DOCUMENTATION OF AN ENDOTRACHEAL TUBE

(75) Inventors: Zev Carrey, Far Rockaway, NY (US); Judah Isaacs, Oceanside, NY (US); Charles K. Huang, Taipei (TW)

(73) Assignee: Innovative Medical Devices, Inc., Oceanside, NY (US)

( * ) Notice: Subject to any disclaimer, the term of this patent is extended or adjusted under 35 U.S.C. 154(b) by 0 days.

(21) Appl. No.: 12/375,821

(22) PCT Filed: Aug. 7, 2007

(86) PCT No.: PCT/US2007/075360
§ 371 (c)(1),
(2), (4) Date: Jan. 30, 2009

(87) PCT Pub. No.: WO2008/019367
PCT Pub. Date: Feb. 14, 2008

(65) Prior Publication Data
US 2009/0322867 A1  Dec. 31, 2009

Related U.S. Application Data

(60) Provisional application No. 60/836,002, filed on Aug. 7, 2006.

(51) Int. Cl.
*H04N 7/18* (2006.01)
*A61B 1/04* (2006.01)
(52) U.S. Cl. .......................... 348/77; 600/109
(58) Field of Classification Search ............... 348/41, 348/61–77; 600/101, 109, 112, 121–122, 600/175
See application file for complete search history.

(56) References Cited

U.S. PATENT DOCUMENTS

| 4,742,819 A | 5/1988 | George |
| 4,846,153 A | 7/1989 | Berci |
| 5,257,636 A * | 11/1993 | White ........................ 128/897 |

(Continued)

FOREIGN PATENT DOCUMENTS

| WO | 2004030527 | 4/2004 |
| WO | 2005099802 | 10/2005 |

OTHER PUBLICATIONS

David Brinn. "Israel's Seeing-Eye Endotracheal Tube" The Jewish Press, p. 96, Mar. 25, 2005.
"Tracheoscopic Ventilation Tube (TVT)" Unimedical Biomedical Technologies, retrieved from http://www.unimedical.it/NEWS/news_eng.htm on May 8, 2006.
"Airway Visualization" EZC Medical LLC, retrieved from http://web.archive.org/web/20060308180001/http://ezcmedical.com/intubaid.shtml on Dec. 27, 2006.

(Continued)

*Primary Examiner* — Joshua Joo
(74) *Attorney, Agent, or Firm* — Katten Muchin Rosenman LLP

(57) ABSTRACT

A hand held intubation camera device including a hand held display unit, the display unit including a trigger for actuating a camera. The device also including a disposable stylet connectable to the display unit, the stylet including a camera element formed at a distal end operable by the hand held display unit, and a light emitting element. The device also including a single use interconnect preventing a disposable stylet from being reinserted into the hand held display unit once removed following an initial use.

29 Claims, 25 Drawing Sheets

U.S. PATENT DOCUMENTS

| | | | |
|---|---|---|---|
| 5,363,838 | A | 11/1994 | George |
| 5,676,635 | A | 10/1997 | Levin |
| 5,730,701 | A * | 3/1998 | Furukawa et al. ............ 600/127 |
| 5,827,178 | A | 10/1998 | Berall |
| 5,842,973 | A | 12/1998 | Bullard |
| 6,322,498 | B1 | 11/2001 | Gravenstein et al. |
| 6,458,094 | B1 * | 10/2002 | McMahon et al. .............. 604/35 |
| 6,549,794 | B1 * | 4/2003 | Nadeau et al. ................ 600/310 |
| 6,651,669 | B1 * | 11/2003 | Burnside ....................... 128/897 |
| 6,652,453 | B2 * | 11/2003 | Smith et al. ................... 600/188 |
| 6,655,377 | B2 | 12/2003 | Pacey |
| 6,676,598 | B2 | 1/2004 | Rudischhauser et al. |
| 6,840,903 | B2 | 1/2005 | Mazzei et al. |
| 7,382,231 | B2 * | 6/2008 | Blumberg ................ 340/309.16 |
| 2001/0018918 | A1 * | 9/2001 | Burnside et al. ............. 128/897 |
| 2003/0078476 | A1 * | 4/2003 | Hill ............................... 600/160 |
| 2004/0215061 | A1 | 10/2004 | Kimmel et al. |
| 2004/0260325 | A1 * | 12/2004 | Kuhr et al. ..................... 606/181 |
| 2005/0024500 | A1 * | 2/2005 | Katayama ................ 348/207.99 |
| 2005/0085690 | A1 | 4/2005 | Tien |
| 2005/0261551 | A1 * | 11/2005 | Couvillon, Jr. ............... 600/118 |
| 2006/0004258 | A1 * | 1/2006 | Sun et al. ...................... 600/160 |
| 2006/0162730 | A1 | 7/2006 | Glassenberg et al. |
| 2006/0173244 | A1 | 8/2006 | Boulais et al. |
| 2006/0180155 | A1 | 8/2006 | Glassenberg et al. |
| 2007/0049794 | A1 | 3/2007 | Glassenberg et al. |
| 2007/0085686 | A1 * | 4/2007 | Oz ............................. 340/572.8 |
| 2007/0097090 | A1 * | 5/2007 | Battles .......................... 345/173 |
| 2009/0030405 | A1 * | 1/2009 | Quick et al. ...................... 606/1 |
| 2009/0082630 | A1 * | 3/2009 | Tulley ........................... 600/160 |
| 2010/0121191 | A1 * | 5/2010 | Ariff et al. .................... 600/437 |

OTHER PUBLICATIONS

"Airway Visualization" EZC Medical LLC, retrieved from http://web.archive.org/web/20060520185053/http://ezcmedical.com/intubaid.shtml on Dec. 27, 2006.

"Endotracheal Management" ETView Ltd., retrieved from http://www.etview.com on Feb. 14, 2006.

"Tracheoscopic Ventilation Tube (TVT) System", ETView Ltd., retrieved from http://www.matimop.org.il/newrdinf/hamama/08041.htm on May 8, 2006.

M. Weiss, et al. "Subglottic Video-airway Imaging" The Internet Journal of Anesthesiology. 1998, vol. 2 No. 3, retrieved from http://www.ispub.com/ostia/index.php?xmlFilePath=journals/ija/vol2n3/s . . . on Apr. 19, 2005.

"Airtraq Optical Laryngoscope" retrieved from http://www.airtraq.com/airtraq/portal.portal.action on Jun. 6, 2007.

International Search Report and Written Opinion dated Jul. 30, 2008 from the corresponding PCT/US2007/075360.

* cited by examiner

SYSTEM TO AID IN THE POSITIONING, CONFIRMATION AND DOCUMENTATION OF AN ENDOTRACHEAL TUBE

CROSS REFERENCE TO RELATED APPLICATIONS

The instant application claims the benefit of U.S. provisional application 60/836,002, filed on Aug. 7, 2006, the disclosure of which is incorporated herein by reference.

FIELD OF THE INVENTION

The present invention relates to a system to aid in the positioning, confirmation and documentation of an endotracheal tube in general, and more particularly to a disposable stylet connected to a display and storage device that is inserted within an endotracheal tube to aid in proper positioning, confirmation and documentation of the endotracheal tube within a patient.

BACKGROUND

Intubation is a medical procedure in which an endotracheal tube (hereinafter "ET") is positioned into the trachea, effectively bypassing the mouth, nose and throat, to provide oxygen directly to the lungs. Intubation is a common procedure performed on any person who cannot manage their own airway. In a hospital setting, this includes people receiving general anesthetic in preparation of surgery, but also includes many emergency situations, where injury and trauma impairs one's airway.

Millions of intubations are performed each year in the U.S. but despite this frequency, complications due to improper or difficult intubations are an all too common occurrence. Injuries as a result of improper intubation account for nearly 25% of all anesthesiology malpractice claims. Failed ET intubations are one of the largest problems facing surgical teams and emergency responders today. Yearly there are hundreds of malpractice lawsuits filed relating to mishaps during intubation. Many of these lawsuits are quite serious stemming from serious injury and even death of the patient.

The insertion of an ET is often accomplished using a laryngoscope, but using a laryngoscope requires skill and proper training. The laryngoscope is inserted into the mouth to push away the tongue and lift the epiglottis so that a view of the glottis (space between the vocal cords) is possible. The goal is then to feed the ET into the airway and the trachea instead of the esophagus (which is located directly behind the trachea), and then to maintain such placement during patient transport or until the ET is removed. If the ET is mistakenly placed in the esophagus the mistake can be fatal or lead to brain injury and permanent disability. Statistically, about 8% of all intubations are difficult, which leads to an increased chance of improper intubation.

The problem is that even when a patient's mouth is open, even using a laryngoscope, the vocal chords are not visible, and by feeding the ET into the airway, even visual inspection of the glottis becomes blocked. Even if properly placed, a problem may still occur when proper placement of the ET is re-checked following placement for example, when patients are transported by ambulance after the patient has been intubated by emergency medical services, where the movement might have dislodged, or partially dislodged the ET.

There are generally three types of instruments that have been utilized to provide video assisted tracheal intubation. The first is the ET itself, the second is the laryngoscope blade, and the third is an intubation stylet, i.e. a device which is slid through the center of the ET and aids in the insertion of the ET into the airway. In each case, an image is transmitted, usually via fiber optic material or the like, from the tip of the instrument to a display that is visible to the doctor during use of the instrument.

With respect to the first two types of instruments, namely the ET and the laryngoscope blade, these generally tend to be modifications of the regularly utilized instruments. Specifically, some form of ultra thin fiber optic is integrated into the instrument which feeds to a display monitor at the end of the instrument or remote of the instrument. Such video-intuboscopy and video laryngoscopy have generally been utilized in hospital settings where extensive monitor equipment is available. Such devices have provided limited, if any, assistance to first responders such as EMS personnel. The video-optical intubation stylet that has been suggested also uses optical fibers for image transmission from the stylet tip to the video camera monitors. However, these also require remote imaging and provide difficult video monitoring, especially in emergency response conditions.

It has also been recently suggested to use video electronics, such as a miniature electric camera which is incorporated in the distal end of the endotracheal tube itself or the stylet. However, no practical implementation of such device has been suggested and no suitable display mechanism has been provided to facilitate usage by emergency responding personnel. Furthermore, most of these devices that have been suggested provide complex structure with inadequate monitoring for the convenience of the medical personnel utilizing such instruments.

SUMMARY OF THE INVENTION

A stylet for an ET comprises a distal end for viewing the position of the stylet or ET, and a proximal end for connection to a display and storage device. The distal end is preferably equipped with a light, a lens and means for translating visuals into electronics, such as, for example, a charged coupled device (CCD) or a sensor complementary metal oxide semiconductor (CMOS) device. The proximal end of the stylet is preferably equipped with a connector for connection to a display and storage device that allows for viewing the visuals experienced at the distal end. Thus, the distal end of the stylet is provided with one portion of an electronic camera, i.e., the portion that captures visuals, while the proximal end of the stylet is connected to a display and storage device that constitutes the other portion of an electronic camera, i.e., the portion that displays and stores the captured visuals. This splitting of the electronic camera function into a relatively inexpensive component (stylet) and a relatively expensive component (display and storage device) renders the stylet disposable, and allows for the use of a new, sterile stylet with each new procedure. This is also beneficial because the stylet is usually the only component of the system that makes contact with the patient and therefore there is no need to undergo the added expense of sterilizing the stylet if it can be disposed of instead.

The display and storage device is preferably comprised of a handgrip that is coaxial with a connected stylet, and a display connected to the top of the handgrip, such that the display is angled in preferably two directions with respect to the axis of the handgrip. With this orientation, peering into the display is easily viewed while handling with one hand and permitting insertion of the stylet through the ET and into the patient with the other. Thus, the user's gaze is directed toward the patient and the ET and, at the same time on the display, which improves focus and coordination of the entire procedure as all instruments are within the user's view. The display and storage device is further equipped with a recording feature for recording the procedure if desired either as still photos or as a video clip, both which can be taken by a camera element in the stylet, and an output device for connecting the display and storage device to another device. Preferably, the display and storage device is provided with a USB port or the like for exporting captured footage to a computer or the like.

Another aspect of the present invention is a hand held intubation camera device including a hand held display unit, the display unit including a trigger for actuating a camera. The device also including a disposable stylet connectable to the display unit, the stylet including a camera element formed at a distal end operable by the hand held display unit, and a light emitting element. The device also including a single use interconnect preventing a disposable stylet from being reinserted into the hand held display unit once removed following an initial use.

DETAILED DESCRIPTION OF THE PREFERRED EMBODIMENTS

Figure 1:
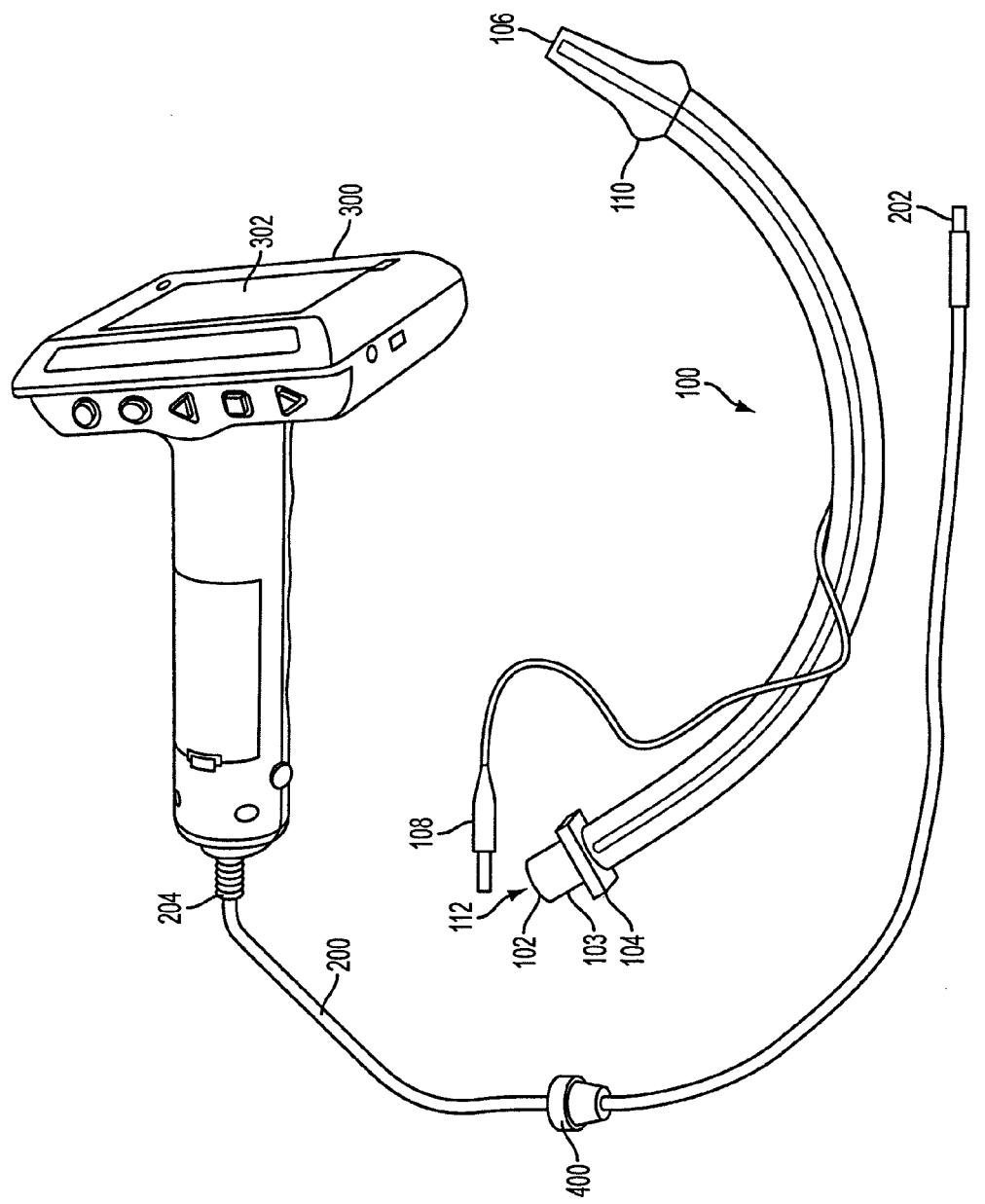
FIG. 1 depicts a hand held camera device, a stylet and an endotracheal tube according to one aspect of the present invention.

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

FIG. 1 shows an endotracheal tube (ET) 100 for insertion into a patient. Though a variety of sizes are known to those of skill in the art a single size is shown here and the invention described herein is alternatively usable with any of the other sizes without departing from its scope.

The ET includes a proximal end 102, which remains outside the patient upon insertion. The proximal end 102 includes a port 103 which receives a stylet 200. The port 103 is formed with a tab 104 for manipulation of the ET 100 and allow for easier grasping of the ET during use. The ET 100 includes a distal end 106. The proximal end 102 and distal end 106 are connected via a lumen, and both ends have openings therein to allow for passage of a stylet, as will be discussed below, and allows for the passage of oxygen following insertion. The distal end 106 has a balloon cuff 110 near the distal end to secure the ET in the trachea of a patient. The balloon cuff 112 is inflated by an inflation line 108 which is connected to a pressurized air or oxygen source (not shown).

FIG. 1 shows a disposable stylet 200. The stylet 200 include a distal end 202, including an illumination source, and a camera for viewing the insertion of the ET 100. On a proximal end 204 is a single use lock out mechanism that will be discussed below. In sliding engagement along the length of the stylet 200 is a length stop 400, which will also be discussed in detail below. The stylet 200 is preferably made out of malleable or semi-malleable material so that it can flex or alter its shape as it passes into the ET 100 to accommodate the needs and biology of the patient. The stylet 200 is preferably coated with a silicon material to facilitate passage through the ET 200. The distal end 202, though shown as substantially straight, may optionally be curved to coincide with the curvature of the ET 100, and ease insertion therein.

Figure 2:
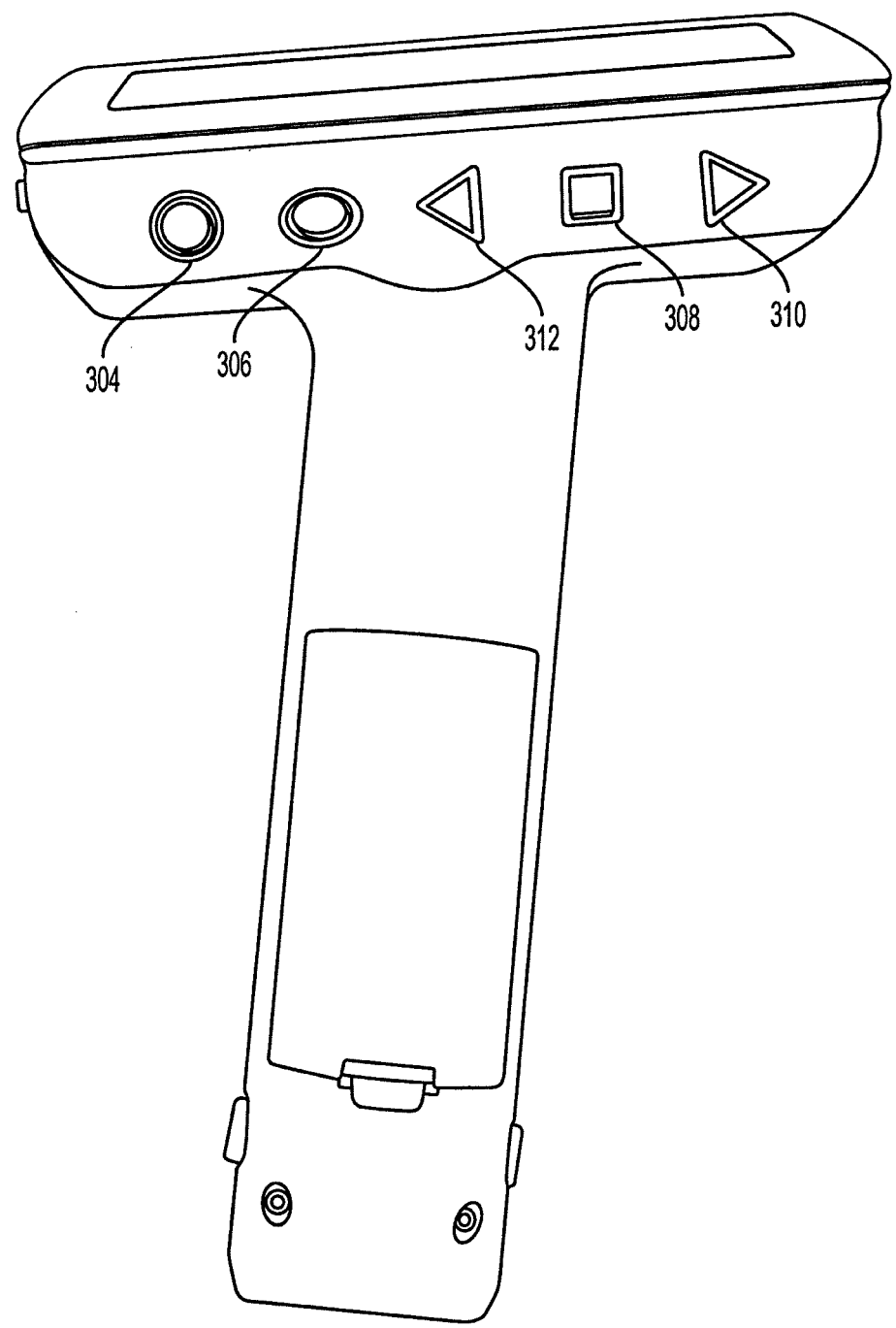
FIG. 2 is a rear view of the hand held camera device of FIG. 1.
Figure 3:
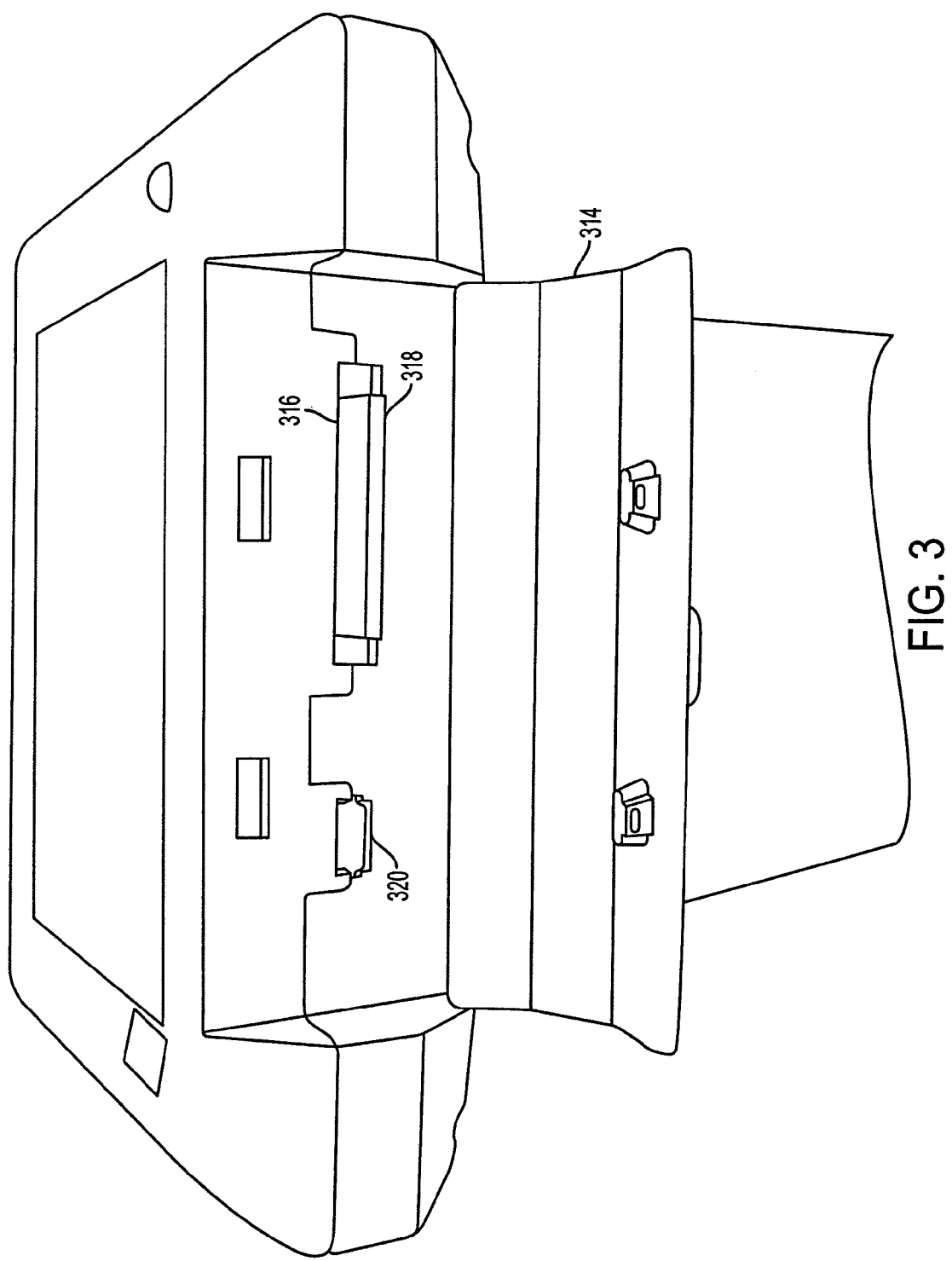
FIG. 3 is a front view of the hand held camera device of FIG. 1, showing a USB port and memory card slot.

FIG. 1 also includes a portable handheld camera display 300. As described above, the stylet 200 includes a camera. Pictures taken by the camera are shown on a display 302. The controls of the handheld camera display 300 is shown in greater detail in FIG. 2. The controls includes a 30-second timer 304, a mode or video button 306, a play button 308, a next button 310 and a back button 312. The buttons can be depressed either by the user's hand not holding the camera display 300, or when occupied, the user's thumb. FIG. 3 shows a cover 314, which protects a recordable media slot 316, in which a recordable media such as SD-ram or other flash memory 318 is inserted. FIG. 3 also shows a USB port for downloading images taken by the camera to a computer.

In addition to still photographs of the positioning of the ET, the handheld camera display 200 and stylet 200 with camera element can be used as a video camera to make video clips of the entire insertion procedure. As will be appreciated the making of video clips requires additional memory of the recordable media, however, this is well within the current state of recording media technology.

To use the camera display 300, a user presses the play button 308. For initial activation, pressing the play button 308 starts the device from an off or suspended state. Pressing the play button 308 the first time causes the last picture taken by the camera and recorded on the recordable medium 316 to be displayed on the display 302.

Modes of operation include a play mode, which displays pictures which have been taken, and a shoot mode, which activates the camera and takes pictures. The Next and Back buttons 310 and 312 are used to scroll through the pictures or video clips on the recordable media.

Figure 4:
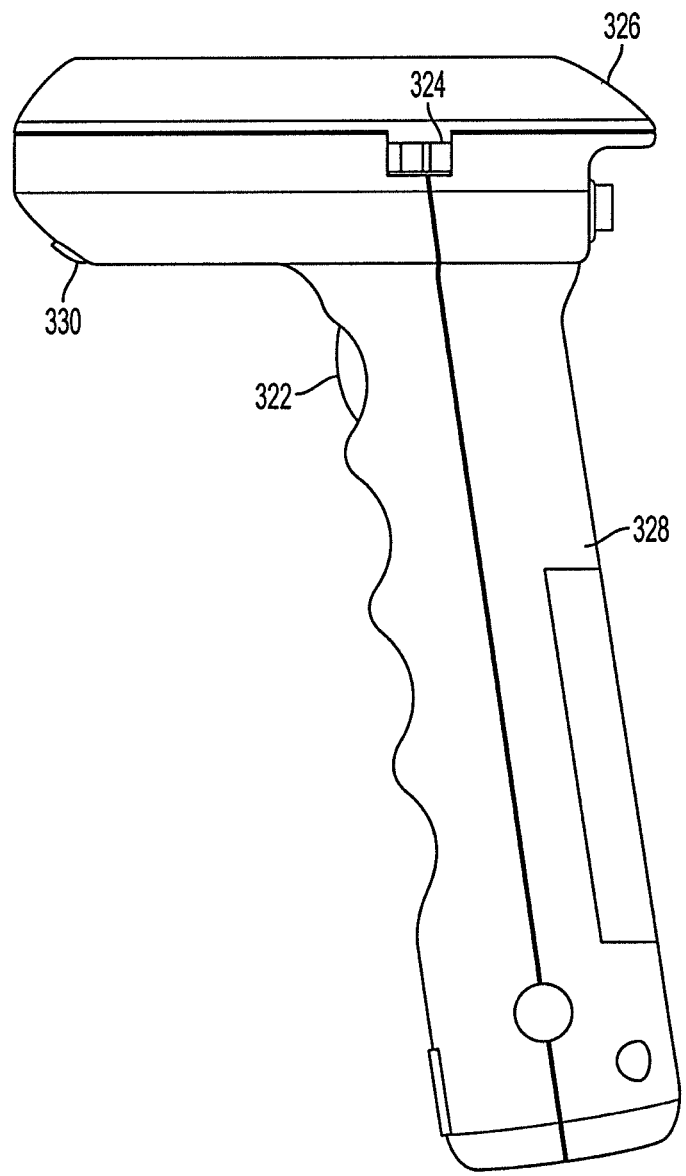
FIG. 4 is a side view of the hand held camera device of FIG. 1.

Upon taking a photo or video clip, the date, time and if desired other identifiers such as the name or ID of the patient may be added to the photographs or video clips to document the proper placement of the ET 100 in a patient. Under one preferred embodiment, upon depressing the trigger or shoot button 322, shown in FIG. 4 causes a series of six pictures to be taken in succession, at for example a 0.2-15 second delay. This delay may be set by the user, depending upon the procedure being under taken. For example, for initial insertion, in conjunction with the 30-second timer, it may be desirable that the pictures be taken every 5 seconds, to show that placement was proper and timely and within the 30-second time limit for proper intubation. Alternatively, if making a quick check of the placement of the intubation tube before transferring a person from an ambulance to a gurney for movement into a hospital, a faster time period may be desired. Further the delay may be set by the manufacturer, thus producing a standardized set of photos of video for every intubation procedure. FIG. 4 also shows an on/off switch 324 for turning the device on and off as desired. However, the operating system of the device also includes an automatic shut off, which powers down the device if no buttons are pushed in a certain time period, for example, for a period of two minutes.

The 30-second timer is useful for the practitioner, as it has been determined that 30 seconds is an optimal time period for insertion of an ET. Taking longer can result in a lack of oxygen to the patient. One method in the past that has been taught to medical personnel is to hold their own breath, during the insertion. However, this is imprecise, to say the least, and can cause the medical personnel to rush the insertion. The 30-second timer provides a better alternative, and with the inclusion of alarms at various timings including 15, and 5 seconds, or at other desirable time periods, the medical professional can accurately gauge their progress in the insertion of the ET 100.

Another feature of the present invention is that the orientation of the portable handheld camera display 300. First, in FIG. 4, the top portion 326 of the device 300 has an angle to the handle 328 of approximately 110 degrees. That is the top portion 326 and the handle 328 are at an angle to each other of approximately 20 degrees greater than perpendicular. This causes the display 302, to be angled in the direction of the user, when the user grasps the handle 328 in a manner such that the user's index finger is positioned over the trigger 322.

Figure 5:
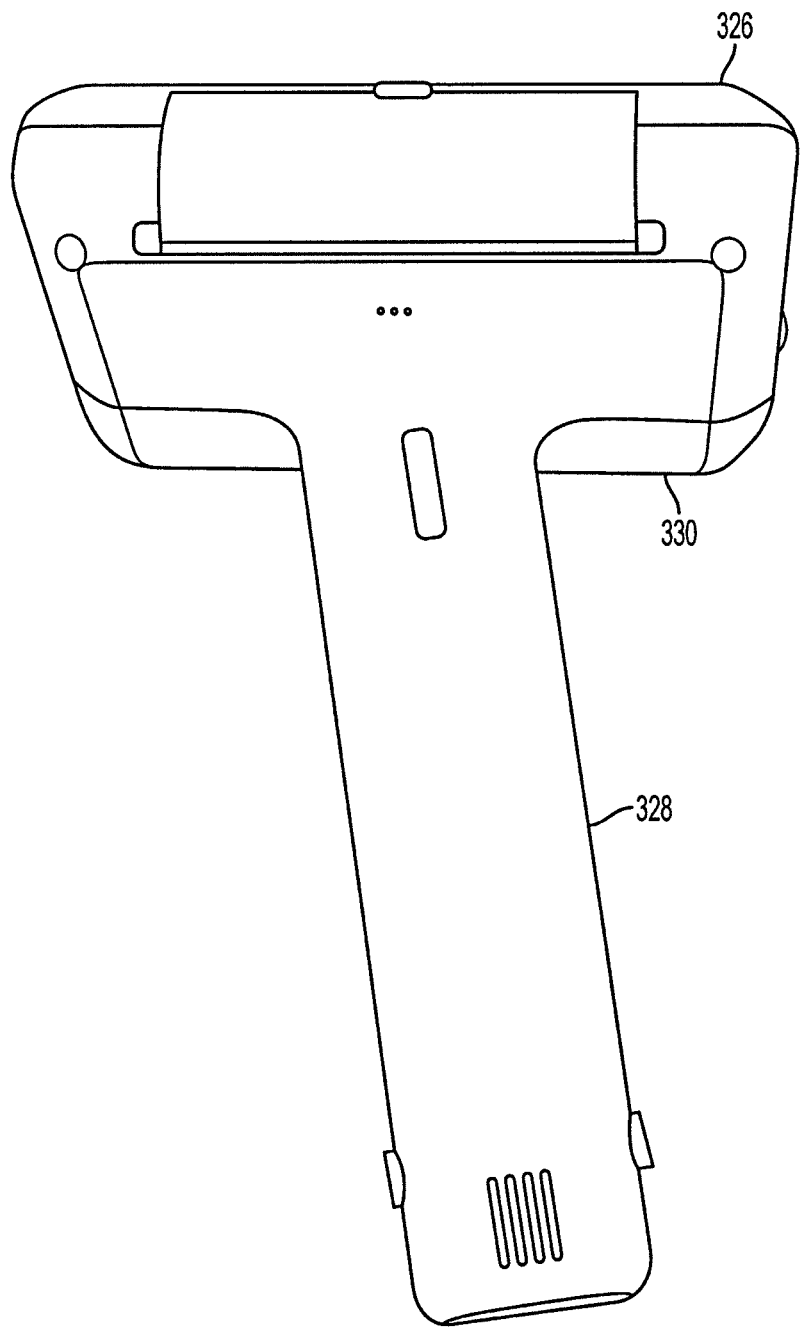
FIG. 5 is a front view of the hand held camera device of FIG. 1.

In addition to the angling upwards of the display 302 in relation to the handle. As shown in FIG. 5, the bottom portion 330 and top portion 326 are also angled with respect to the handle 328. FIG. 5 shows approximately a 20 degree angle, that is when looking at FIG. 5 the handle 328 appears to be angled to the right approximately 20 degrees. This results in the display 302 being not only angled up but also to one side, both of which allow for better viewing of the display during insertion. Other angles of orientation may be incorporated into the device without departing from the scope of the present invention.

Figure 6:
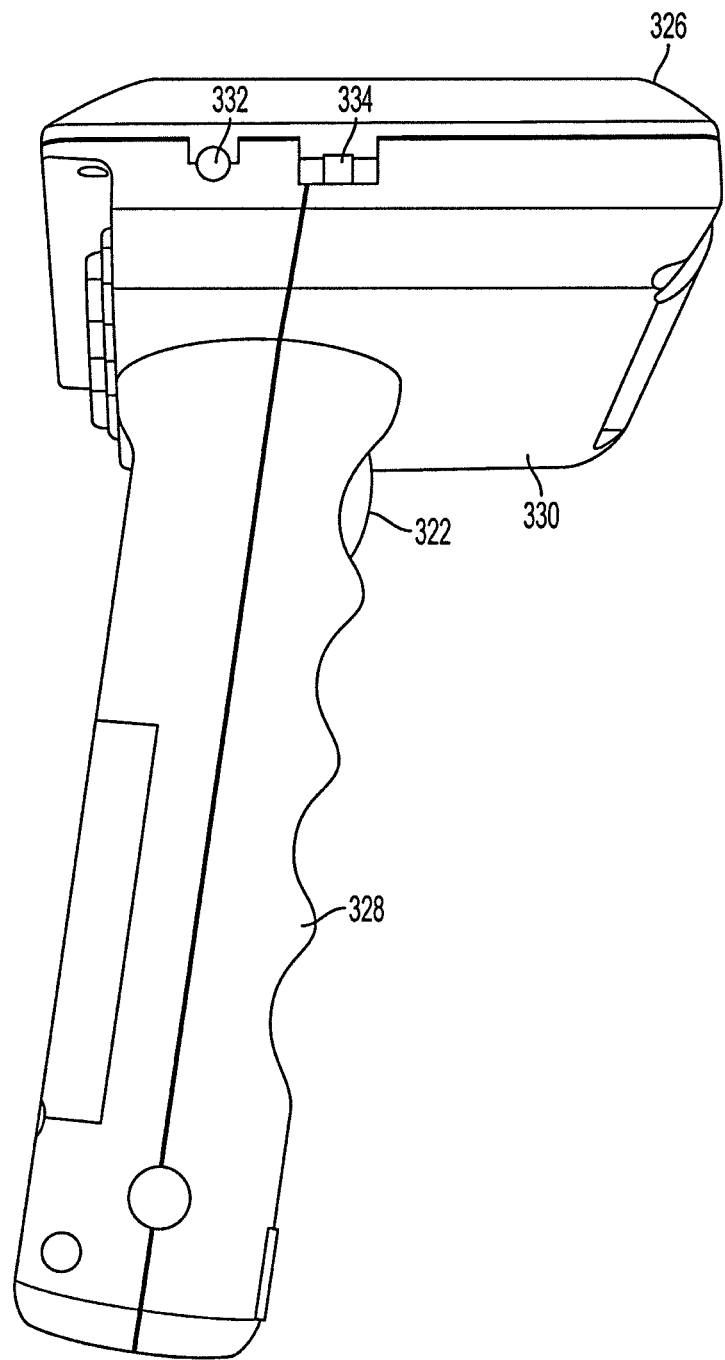
FIG. 6 is a side view of the hand held camera device of FIG. 1.

FIG. 6 shows another side view of the camera display 300, showing a delete or format button 332, which can be used to delete images from the recording medium 318. FIG. 6 also shows a brightness switch 334 which is used to control the brightness and intensity of the display 302.

Figure 7:
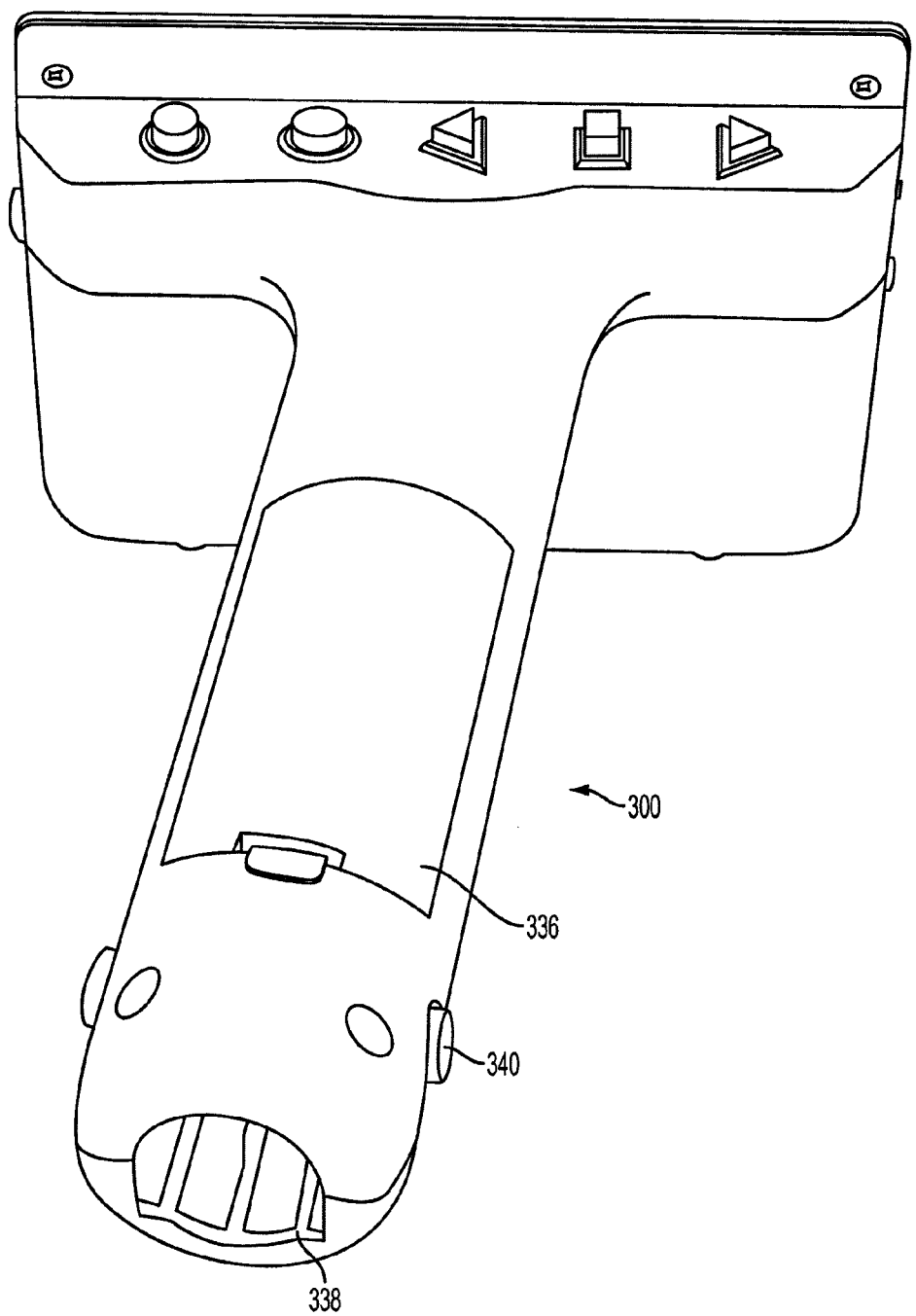
FIG. 7 is a bottom perspective view of the hand held camera device of FIG. 1.

FIG. 7 shows a bottom view of the hand held camera display 300. From this view a battery compartment 326 can be seen, in this compartment batteries, which power the device are stored. It has been found that by keeping the power source in the hand held camera device 300, the size of the distal end 202 of the stylet 200 can be optimally minimized. Also shown in this view are a stylet insertion cavity 338 and stylet release buttons 340.

Figure 8:
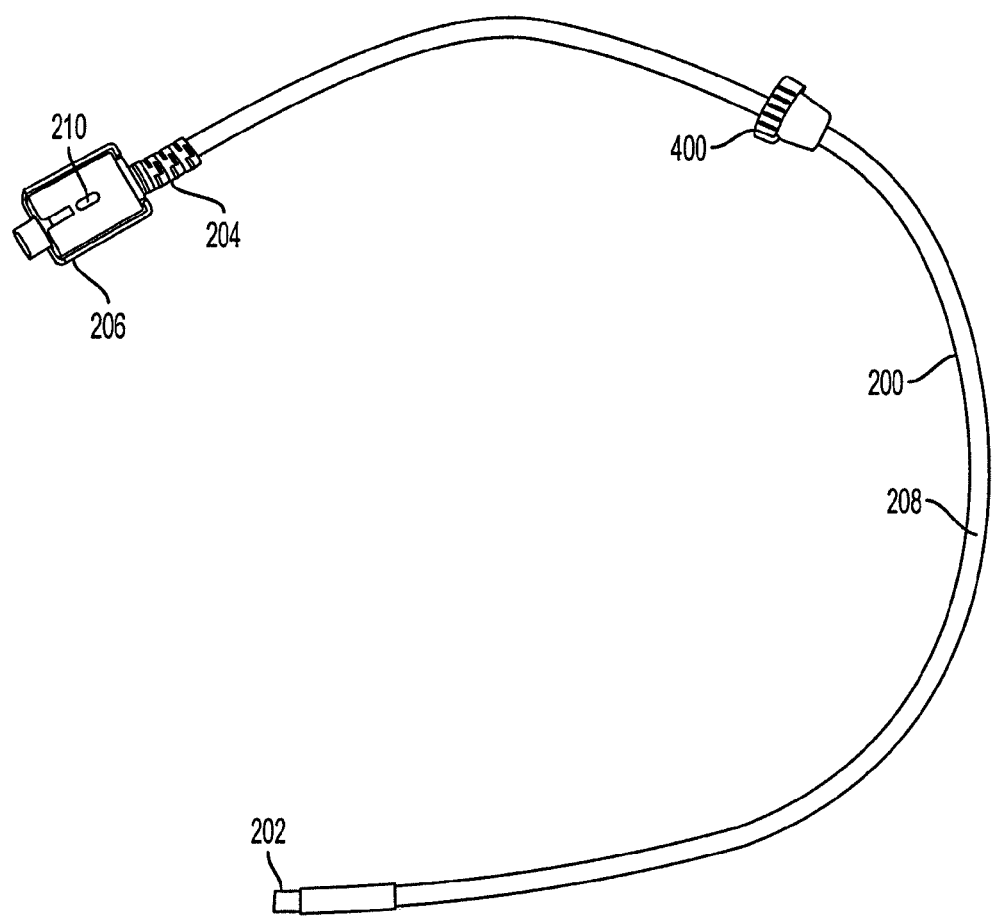
FIG. 8 depicts a stylet according to another aspect of the present invention.

A stylet 200 from FIG. 1 is also shown in FIG. 8. The stylet 200 includes a distal end 202 and a proximal end 204. In use the proximal end, and specifically, an interface 206 is inserted into the insertion cavity 338 of the hand held camera display 300. The battery in the hand held camera display 300 powers a camera element and led lights which are housed in the distal end of the stylet 200. The stylet 200 has wires running inside of the protective coating 208 to connect the distal end 202 with the interface 206 electrically, and therewith the hand held camera display 300.

The interface 206 of the stylet 200 includes a single use lock out mechanism. The single use lock out mechanism 210 may be for example a button 210 on one side of the interface 206. When the stylet is new and unused, the button 210 is in a depressed position. This allows the interface to be inserted into the stylet insertion cavity 338 of the hand held camera display 300. In this position, the stylet 200 and hand held camera display are ready for use, that is, they are ready to be positioned within an ET 100, and to allow viewing of the positioning of the ET and the taking of pictures and/or video of the placement.

Figure 9:
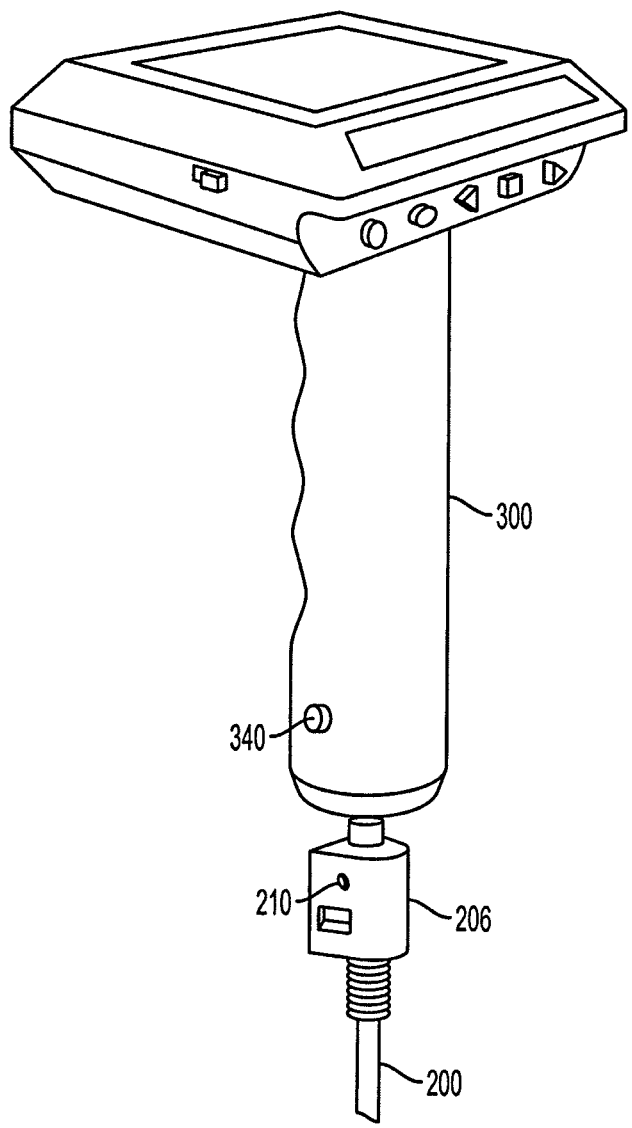
FIGS. 9-11 show insertion of a stylet into a hand held camera device.
Figure 10:
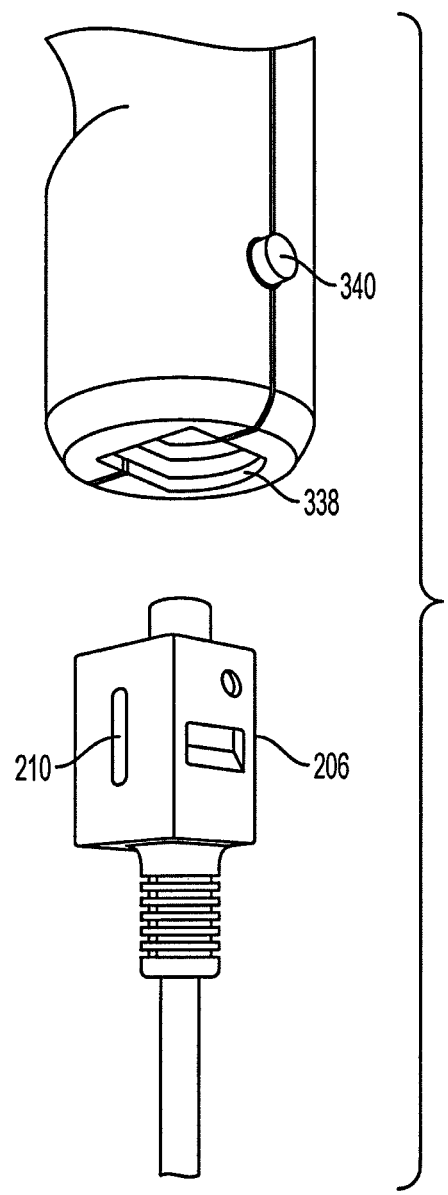
Figure 11:
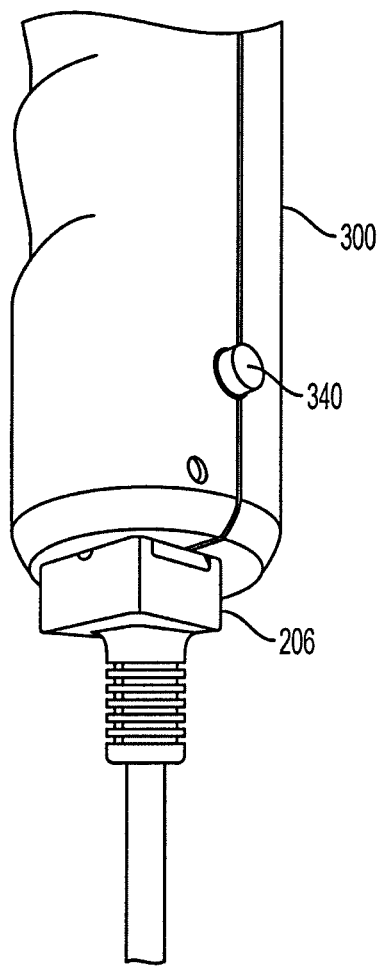
Figure 12:
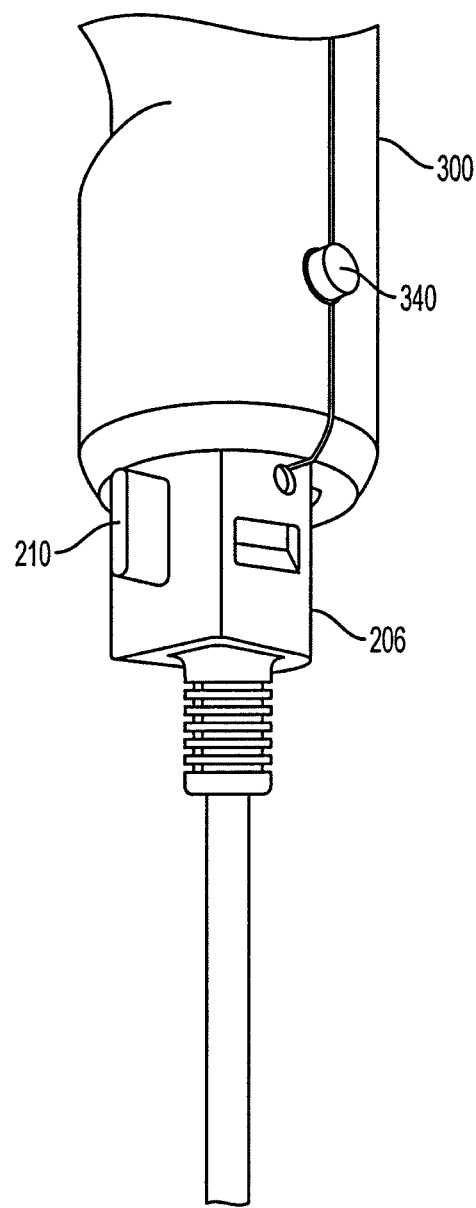
FIG. 12 shows a single use safety guard preventing re-insertion of a stylet following initial use.

Once insertion is completed, or after all uses with a particular patient are completed, the stylet 200 is removed from the hand held camera display 300 by depressing the release button(s) 340, located on either one or both sides of the handle 328. This action causes the button 210 to pop out and create a physical barrier to re-insertion of the stylet 200 into the hand held display device 300. This promotes sanitation and removes the need for sterilization of the stylet, which heretofore was the requirement for re-use. This procedure from insertion through removal of the interface 206 with the hand held camera display 300 is shown in greater detail in FIGS. 9-12. FIG. 9 shows a new stylet 200, with the button 210 not extended being inserted into the base of the hand held camera display 300. FIG. 10 shows the same elements from more of a bottom view. FIG. 11 shows the stylet 200 fitting within the hand held camera display 300. FIG. 12 shows that upon removal, accomplished by depressing the release buttons 340, the button 310 on the interface 206 of the stylet is forced into an extended position. This position effectively prevents re-use of a stylet 200, as it cannot be physically inserted back into the hand held camera device 300.

Figure 13:
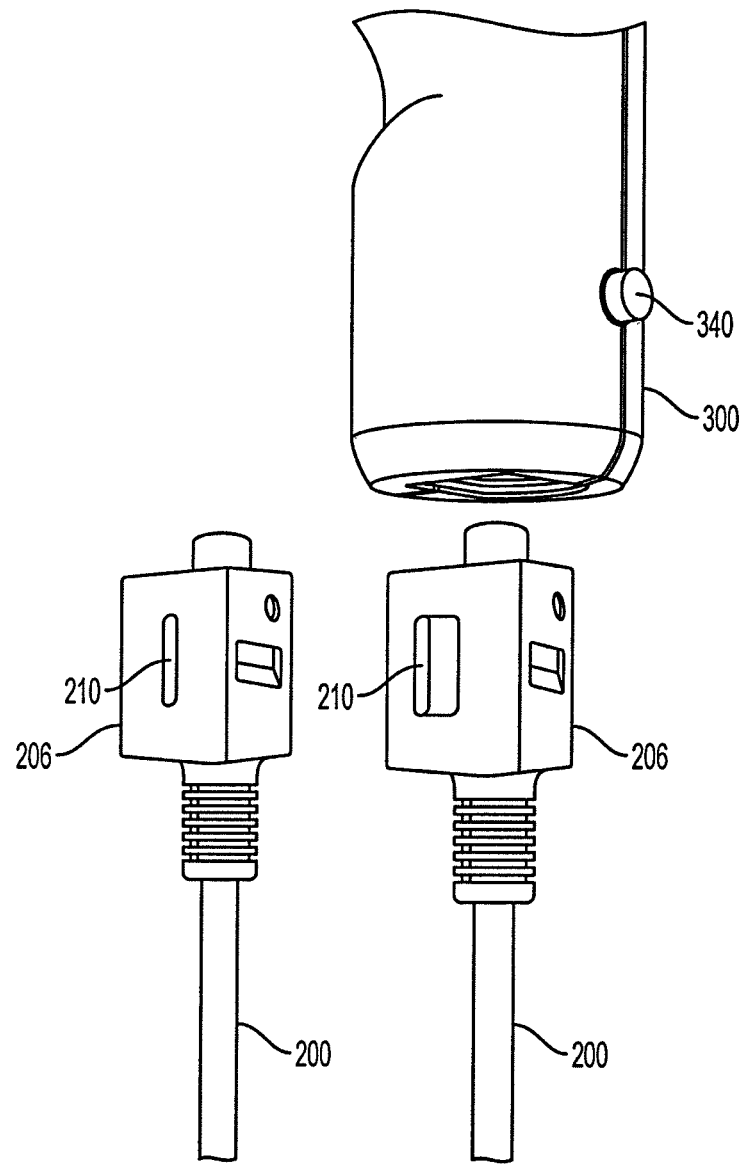
FIG. 13 shows a comparison of new and used stylets.

FIG. 13 shows a sample comparison of interfaces 206 of stylets 200 in a new and a used condition. Though described herein as a button which prevents physical re-insertion of the stylet 200 into the hand held camera display 300, other security devices, to prevent the reuse of the stylets can also be used either singularly or in conjunction with button 210. Other security means could include an identification means in the interface of the stylet, which is recorded by the hand held camera display 300. Following removal if a stylet 200 having such an identifier is reinserted, the hand held camera display 300 will cease to operate unless a different, never used stylet is inserted. Another, method might include, the hand held camera device 300 itself placing an identifier on the stylet 200 such that if that stylet 200 is ever placed into another hand held camera device 300, it too will not operate unless a new and unused stylet 200 is inserted. Other security methods to ensure the single use only aspect of the disposable stylet are also considered within the scope of the instant invention.

Another aspect of the present invention is the length stop 400, shown in FIG. 1. This length stop 400 provides a means of controlling the length of the stylet 200 to be inserted into the ET 100. The length stop 400 is shown in greater detail in FIG. 14. The length stop 400 includes a cap 402 and having a plunger 404. The length stop also includes a body portion 412. The length stop 400 slides over the stylet 200 while the plunger 404 is depressed. Upon determining a desired length of the stylet 200 for insertion into the ET 100, the plunger 404 is released, and a biasing means 406 causes the plunger 404 to impinge on the stylet 200 and substantially prevent the movement of the length stop 400 on the stylet 200.

Figure 15:
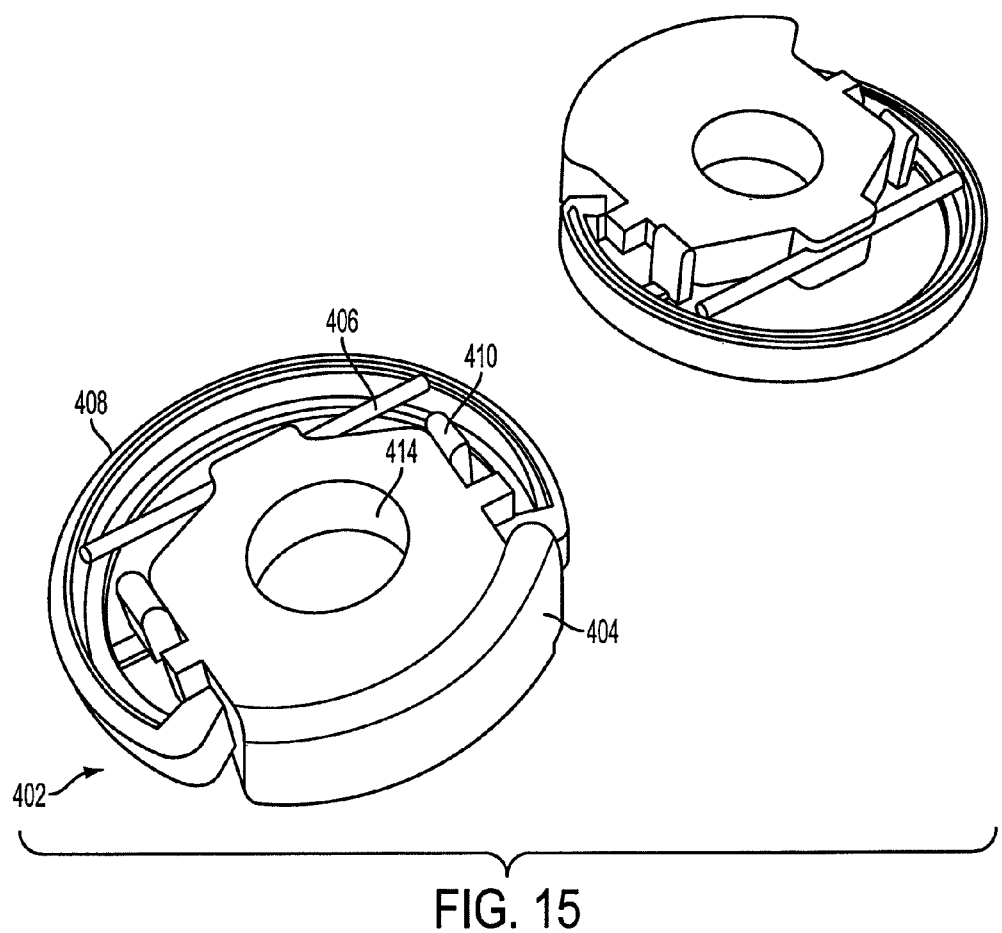
FIG. 15 shows a cap of a length stop.

FIG. 15 shows an internal view of a cap 402 of the length stop 400. The cap 402 includes a stationary portion 408, and the plunger 404. The plunger 404 is biased by the biasing means 406. Both the stationary portion 408 and the plunger 404 include orifices 414. When the plunger 404 is depressed against the biasing means to the point of contacting the stops 410, the orifices 414 substantially align. When the plunger is released, the biasing means 406 causes the orifices 414 to no longer align, and the edges of the orifice in the stationary portion 408 and the plunger 404 each impinge on the stylet 200 and prevent the movement of the length stop 400 on along the stylet 200. In addition, the edges of the orifices may include serrations or ridges to assist in the gripping of the stylet 200.

Figure 14:
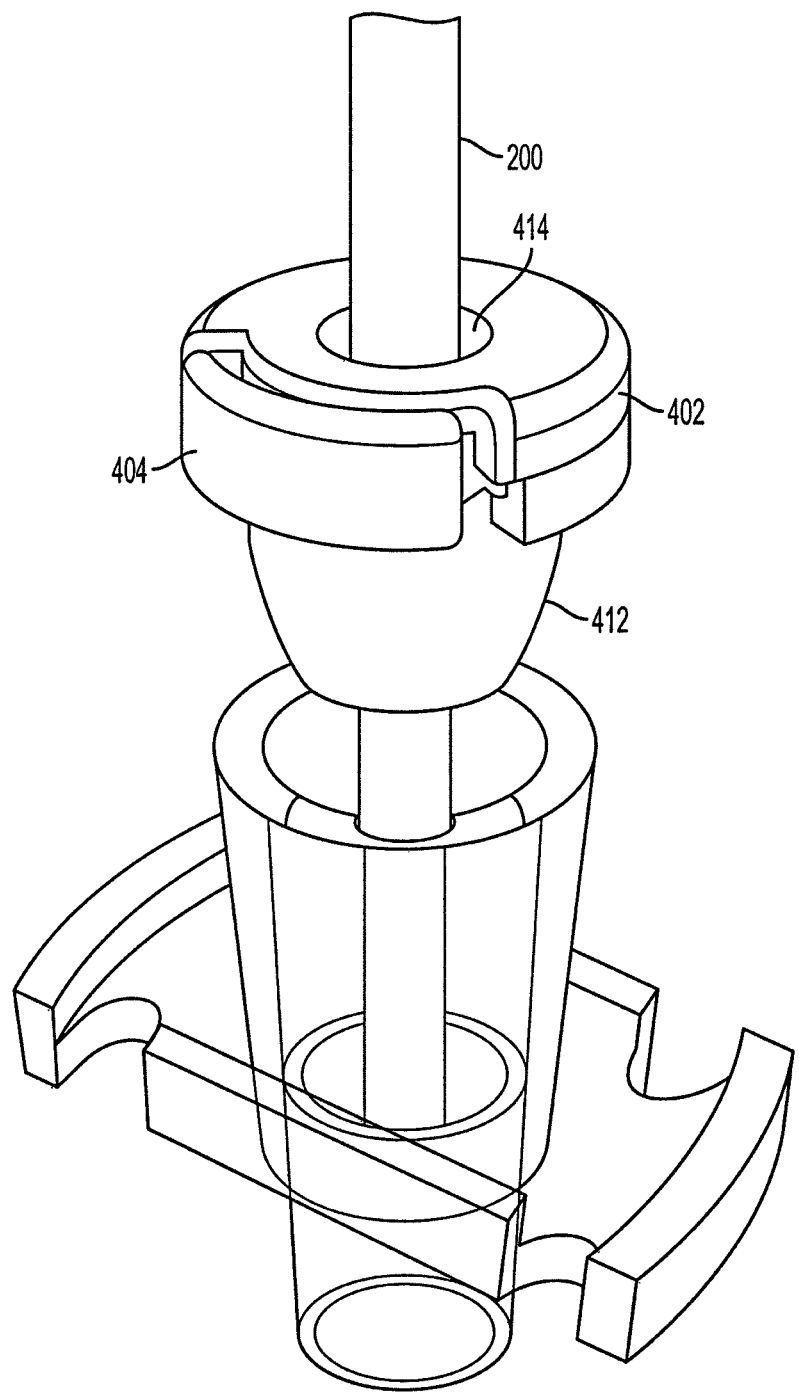
FIG. 14 shows a length stop according to one aspect of the present invention.
Figure 16:
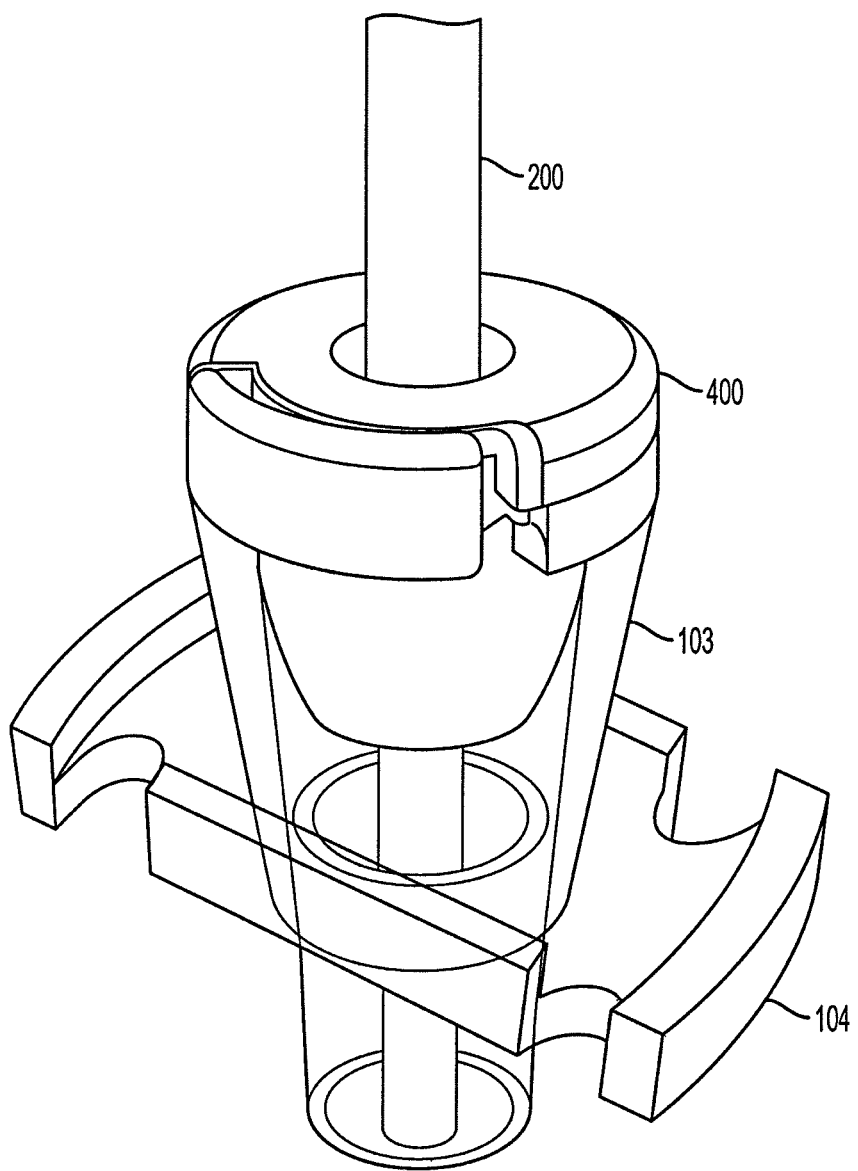
FIG. 16 shows a length stop inserted into a port.

The body 412 of the length stop 400 may optionally have a tapered profile as shown in FIG. 14. This tapered profile allows for ease of insertion of the length stop into the ET 100, as shown in FIG. 16. Specifically the tapered profile of the length stop 400 enables insertion into the port 103, which is formed on the proximal end 102 of an ET 100. This enables a medical professional to set the length of the stylet 200 using the length stop 400, and insert the stylet up to the end of ET 100, and have confidence that this length does not cause the stylet 200 to extend too far or be too short. This reduces the time necessary for insertion of the ET 100 and the taking of pictures using the camera in the stylet 200.

In practice the medical professional may set the length stop 400 on the stylet 200 and insert the stylet 200 into the ET 100 such that the length stop 400 is inserted into the port 103 prior to insertion of the ET 100 into the patient. Alternatively, in some instances it may be desirable to set the length stop 400 on the stylet 200, but not insert the length stop 400 into the port 103, until after the ET 100 is positioned in the patient.

It will also be appreciated that the stylet 200 can be used independent of an ET 100 to image and record other visuals from other locations in the body, and its use and benefit is not dependent on the concurrent use of an ET or other protective covering. Further the stylet 200 and hand held camera device 300 can be used to examine other orifices of the body including the anus, nostrils, ears, etc. Still further, the stylet 200 and hand held camera device 300 may be used in other animals, not just humans. And in another preferred embodiment the stylet 200 may be used in industrial applications as well, for example for inspecting the internal components of an internal combustion engine, or other small spaces, requiring inspection.

To assist in determining this length, the stylet 200 may include markings denoting standard ET 100 lengths, such that a medical professional need only match the known ET 100 size to the corresponding marking on the stylet 200 and set the length stop to that point to ensure accurate insertion of the stylet 200. Other arrangements of a length stop 400 can be envisioned by those of skill in the art, and are considered within the scope of the instant invention.

Figure 17:
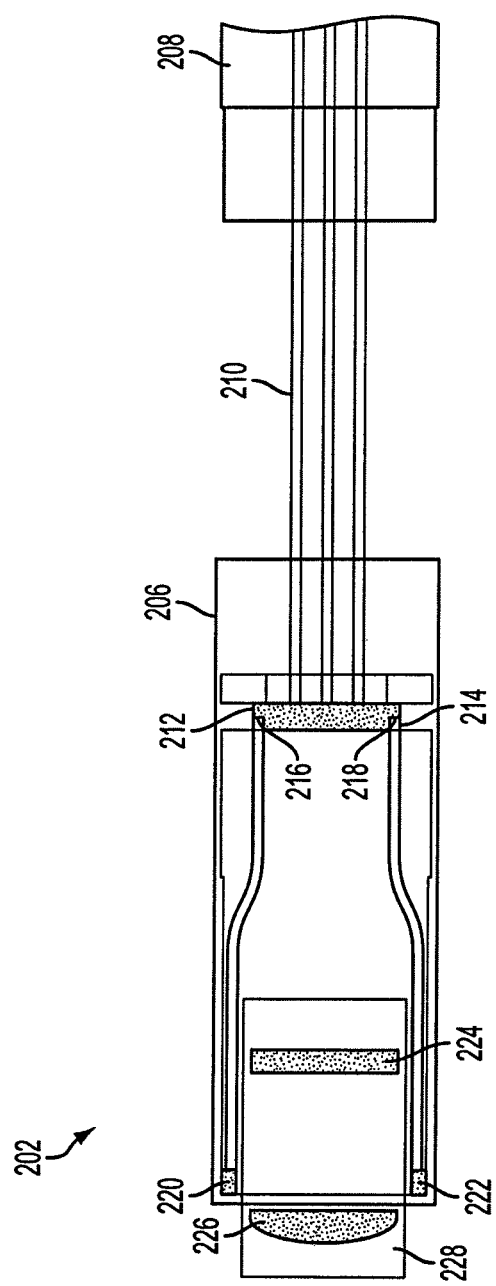
FIG. 17 is a cross-sectional view of a distal end of a stylet according to one aspect of the present invention.

FIG. 17 shows a cross section view of a distal end 202 of the stylet 200 according to one embodiment of the present invention. The distal end 202 includes a first housing 206 and shown separated and extended from the body portion 208 by a plurality of signal and power wires 210. While FIG. 17 shows three wires, it will be understood that other arrangements may be used as needed to transmit either a signal function or a power function or both. Alternatively, a bundle of wires can be utilized to perform the same functions. The wires 210 terminate in a printed control board (PCB) 212 onto which is placed a CCD or sensor CMOS module 214 (hereinafter a CMOS 214 module for purposes of convenience) or the like that functions as a camera component, and a plurality of LED leads 216, 218 that extend to LEDs 220, 222.

Figure 18:
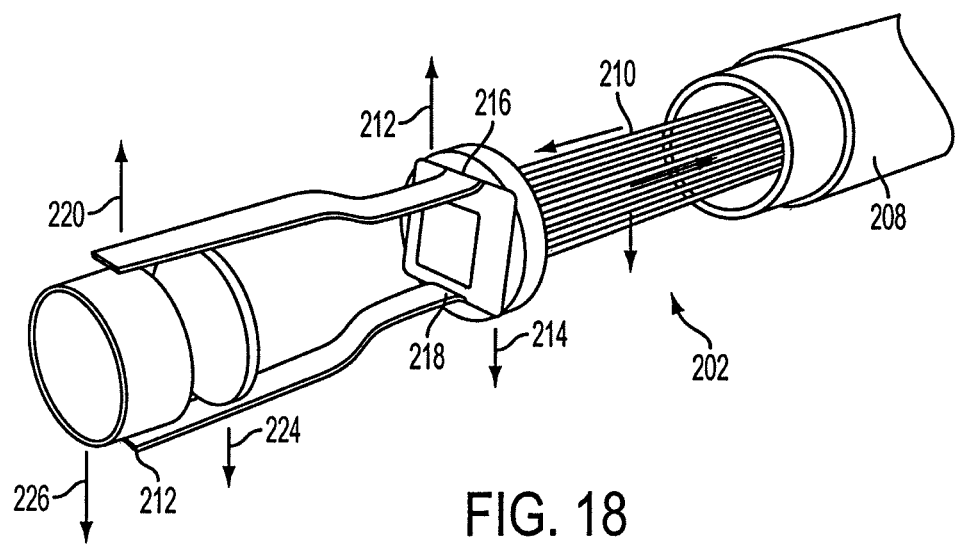
FIG. 18 is an perspective view of a distal end of a stylet shown in FIG. 17.

As shown more clearly in FIG. 18 the LED leads 216, 218 are positioned on either side of the CMOS module 214, which represents an efficient use of space since CMOS devices are typically square and therefore there is room on the side within the circumscribing circle on which the CMOS module 214 is supported so that the leads 216, 218 which connect to LEDs 220, 222 can be connected without requiring additional space.

Figure 19:
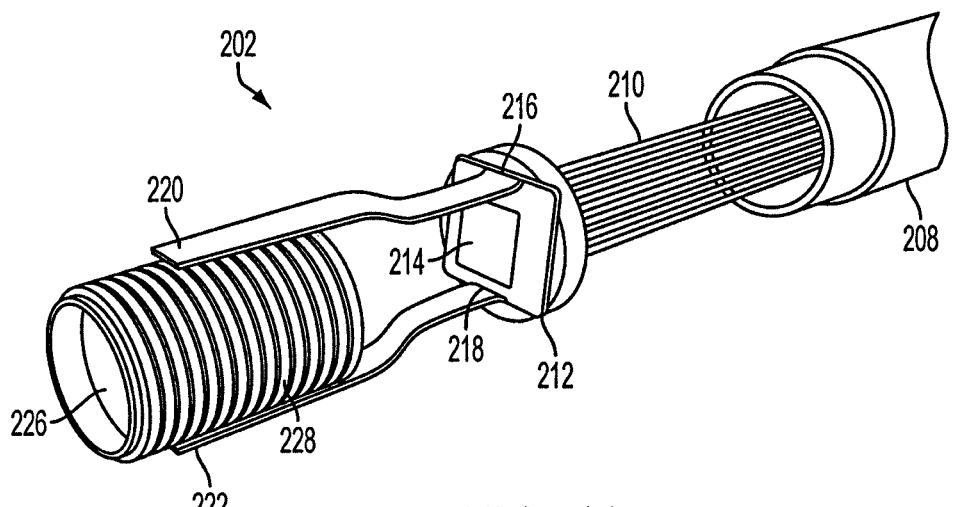
FIG. 19 is an perspective view of a distal end of a stylet shown in FIG. 17.

FIG. 19 shows the plurality of lenses 224 and 226 retained within the second housing 228 that is spaced between LEDs 220 and 222. In operation, the LEDs 220, 222 illuminate images (not shown) that are transmitted through the lenses 226, 224 to the CMOS module 214, which convert the images to electronic signals that are delivered via the signal and power lines 210 through the stylet 200 and are then displayed on the hand held camera display 300 where the electronic signals are converted back to images. While the LEDs 220 and 222 are shown on opposite sides of the CMOS 214, they may also be on two contiguous sides of the CMOS such that the LED's are at right angles to one another.

Figure 20:
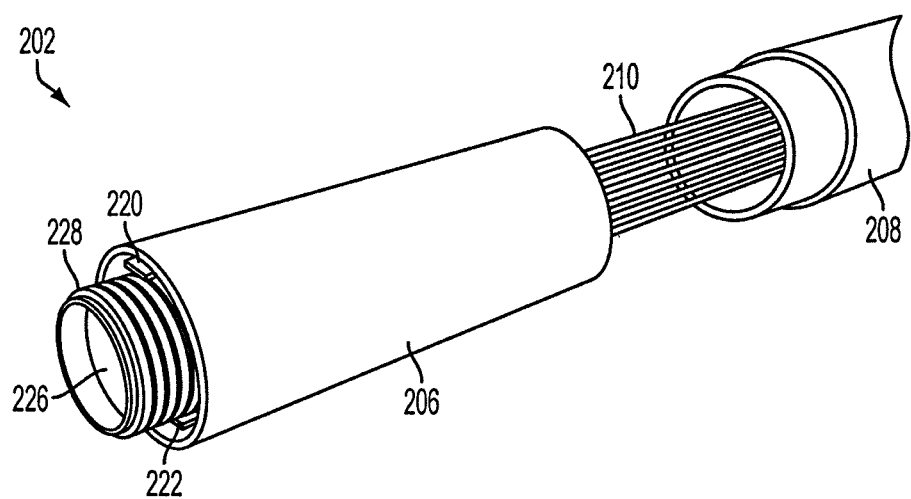
FIG. 20 is an perspective view of a distal end of a stylet shown in FIG. 17.

FIG. 20 shows the lenses 224 and 226 and the second housing 228 inside of the first housing 206, and connected via the wires 210 to the body portion 208 and the remainder of the stylet 200.

Figure 21:
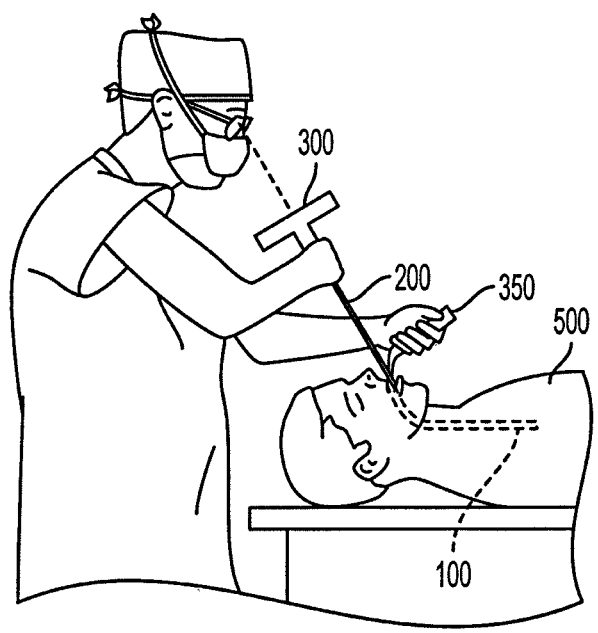
FIG. 21 depicts a medical professional using the hand held camera device and stylet of the present invention to insert an intubation tube in a patient.

With this orientation, as shown for example in FIG. 21 peering into the hand held camera display 300 is akin to peering down the stylet 200 and into the patient 500, since the stylet is directed through the ET 100 and into the patient 500 during use. Thus, the user's gaze is directed toward the patient 500 and the ET 100 and, if used during insertion of the ET 100, the laryngoscope 350 which improves positioning and coordination of the entire procedure as all instruments are aligned within the user's view and the user is not required to divert his or her gaze away from the patient.

The batteries stored under the battery cover 336 provide power to the CMOS module camera component 214 via wires 210 extending through the stylet 200. The hand held camera device 300 could also be provided with an A/C connection to provide A/C power if desired. Wires 210 also connect the camera component with the hand held camera 300. Optionally, the CMOS module camera component 214 could be operably connected to the hand held display device 300 by a remote connection if the system also includes a remote transmitter (not shown) in the stylet 200 and a receiver (not shown) in the hand held display device 300 for receiving video signals from the transmitter. Alternatively, such a system can include infrared technology or the like. The CMOS module 214 and related wireless transmitter (not shown) could also communicate with an alternate display, or other equipment such as remote locations via Bluetooth™ technology. Such communication can also be used to transmit the information via the Internet or the like, thereby facilitating real-time remote incident analysis, advice, assistance, and/or teaching Construction of the stylet 200 in the above-described manner enables the stylet 200 to be disposable. The components used are relatively inexpensive components (i.e. CMOS module, lenses and LEDs), as compared with other stylets currently in use. No fiber optic lines are used preferably such that the stylet 200 is much more flexible that known stylets. Further, by placement of the light source at distal end 202, there is no need to transmit light the length of the stylet 200. The positioning of the CMOS 214 at the distal end 202 of the stylet 200 enables the entire system of the stylet 200 and hand held camera device 300 to operate as a single camera device.

Figure 22:
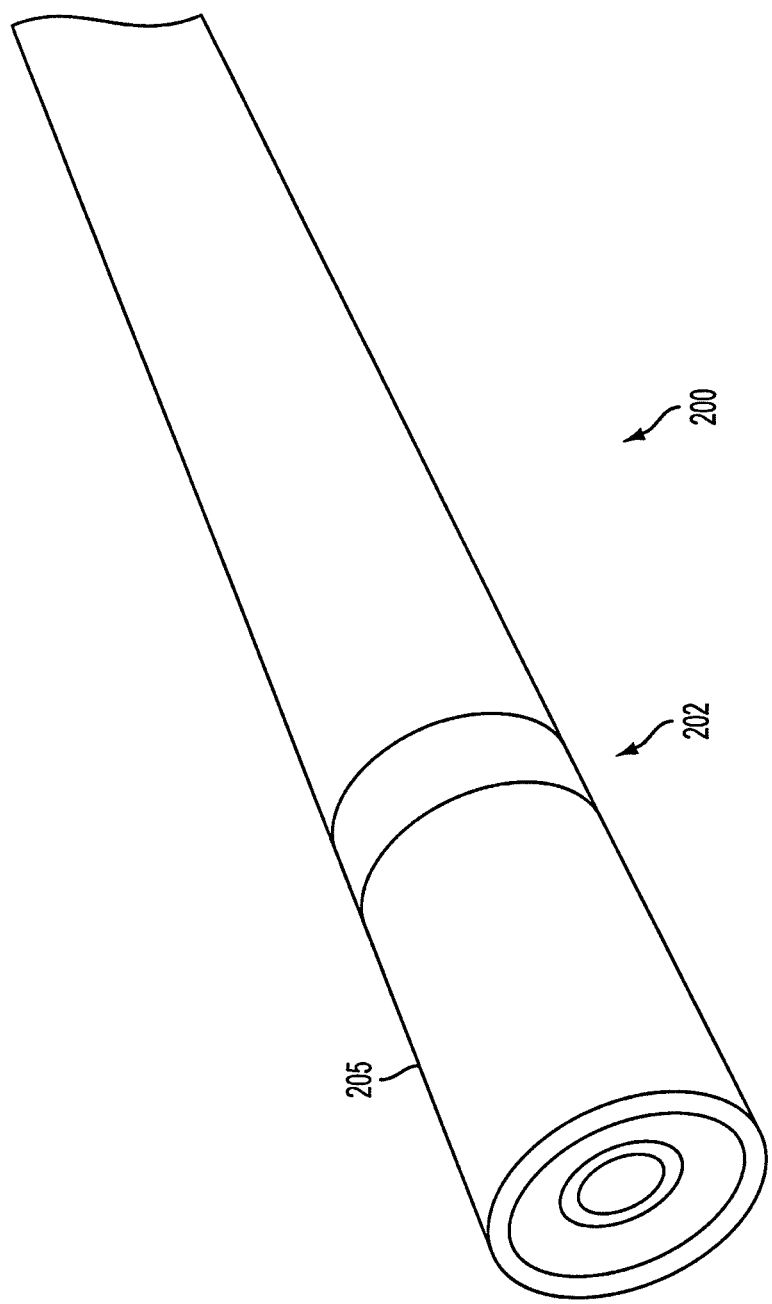
FIG. 22 shows a distal end of a stylet according to another aspect of the present invention.
Figure 23:
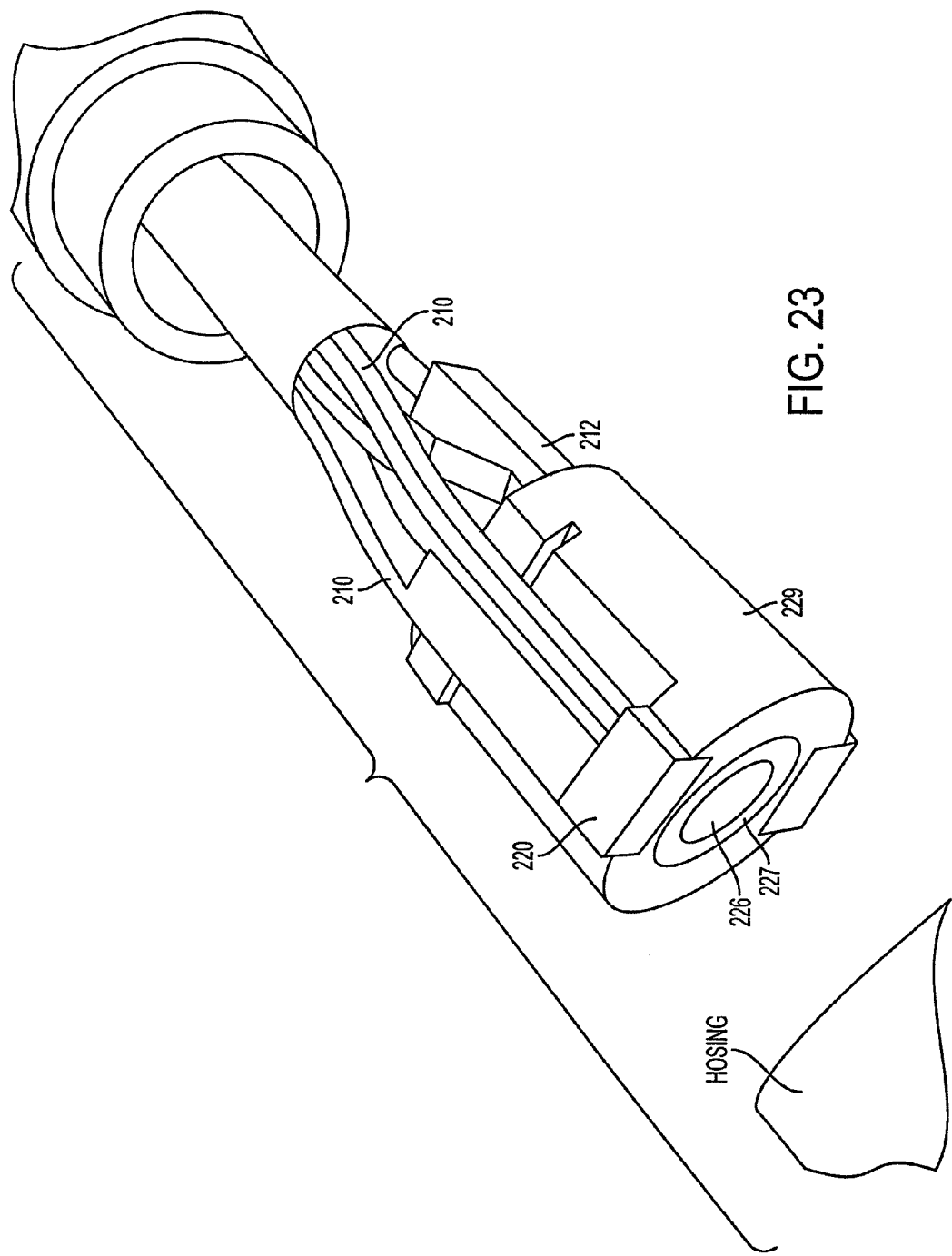
FIG. 23 shows the distal end of the stylet of FIG. 22 with the housing removed.
Figure 24:
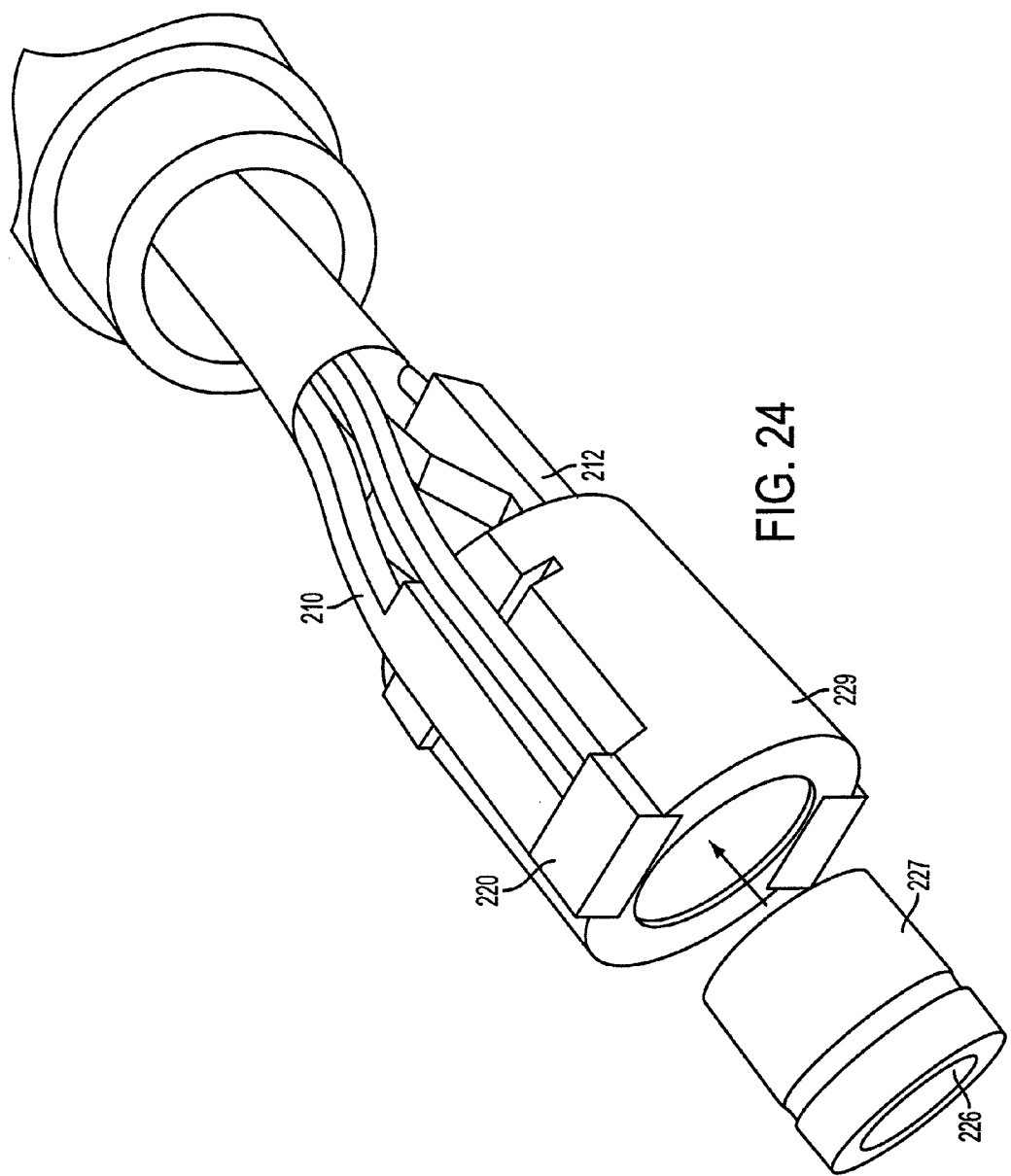
FIG. 24 shows the distal end of the stylet of FIG. 22 with the lens and barrel being removed.
Figure 25:
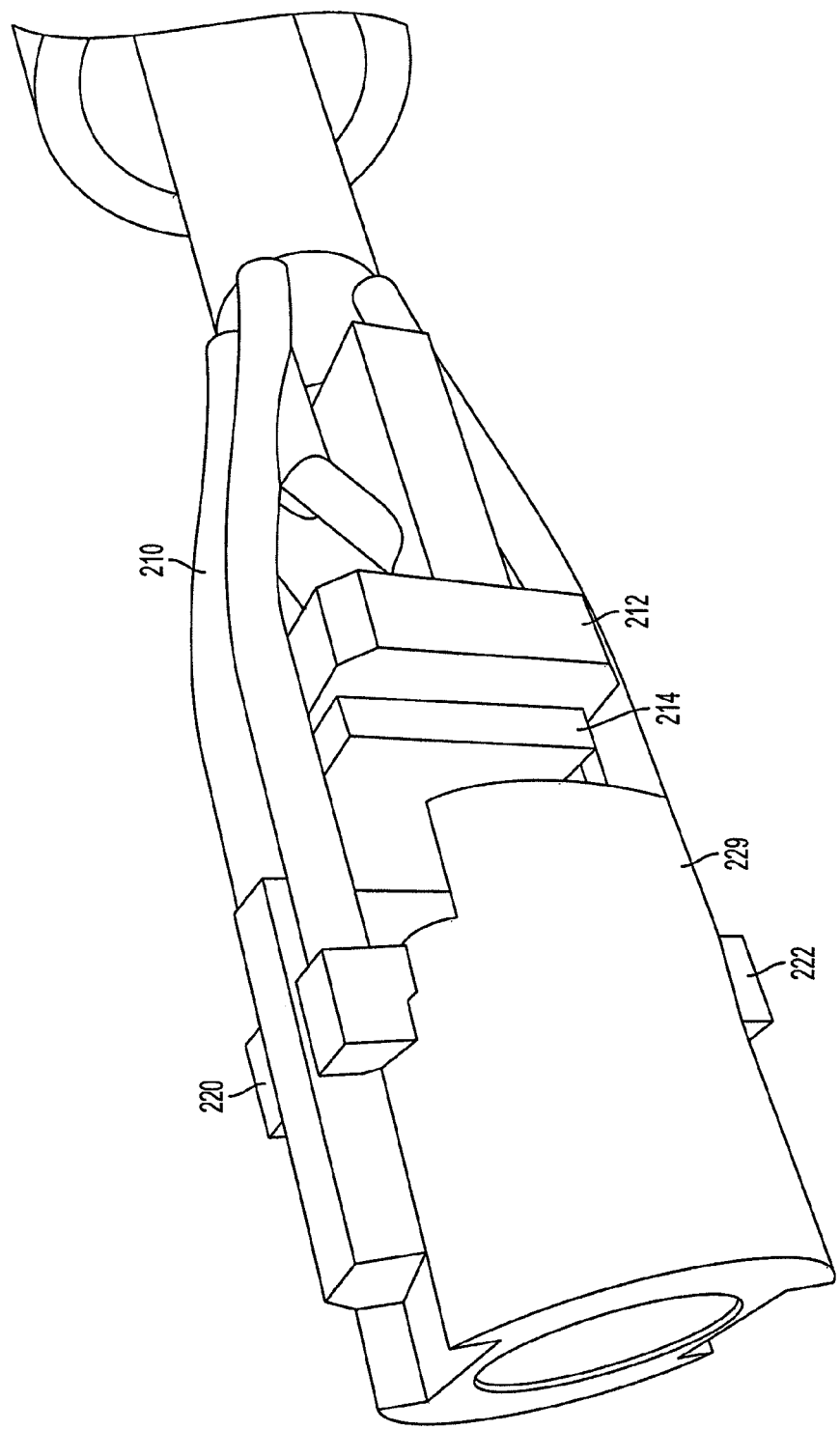
FIG. 25 shows the distal end of the stylet of FIG. 22 with the lens and barrel.
Figure 26:
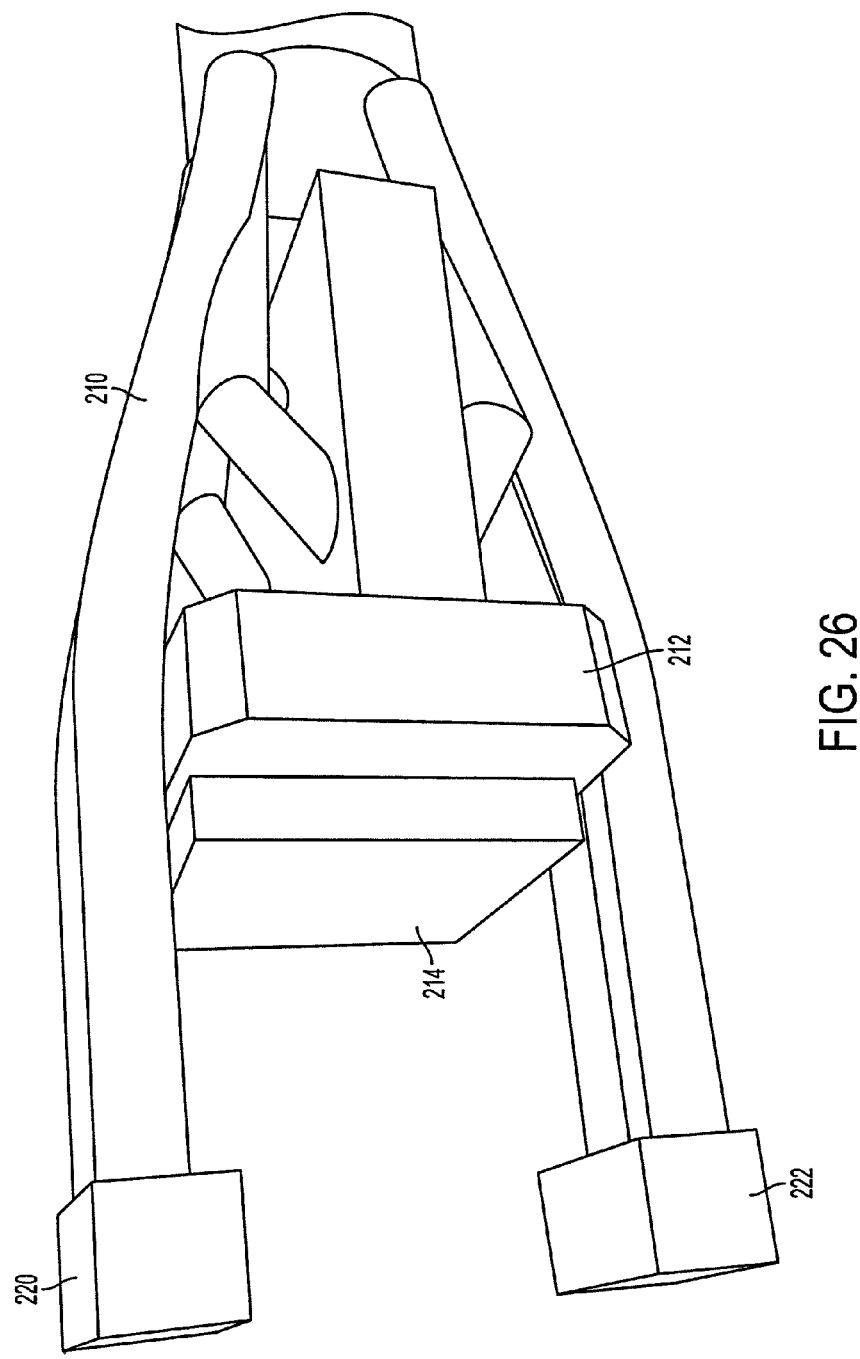
FIG. 26 shows the distal end of the stylet of FIG. 22 with the lens holder removed.

Another orientation of the distal end 202 of the stylet 200 is shown in FIGS. 22-26. In FIG. 22, a distal end 202 of the stylet 200 is shown having a substantially continuous cross section. This helps eliminate the possibility of the stylet 200 becoming lodged in the ET 100. The distal end 202 includes a housing 206 which may be transparent 205. FIG. 23 shows the distal end 202 following removal of the housing 205. In this view the lens 226 is shown formed integrally with a barrel 227. The barrel 227 and lens 226 are inserted into a holder 229. On the top and bottom of the holder 229 are formed LEDs 220 and 222. These LEDs are connected via wires 210 to the hand held camera device 300. In this embodiment there are eight wires 210 used. Two each for each of the LEDs and four which are connected to a T-shaped PCB 212. Unlike the design described above, the LEDs do not connect back to the PCB, but are directly wired to the power source, in the hand held camera device 300. FIG. 24 shows how the integral lens 226 and barrel 227 can be removed from the holder 229. FIG. 25 shows that removal of the holder 229 exposes the CMOS 214, which is formed on a portion of the T-shaped PCB 212. Finally, FIG. 26 shows the holder 229 removed, and the wires 210 coming around the T-shaped PCB 212, on which the CMOS 214 is mounted. It is believed, that by using the smallest CMOS currently sold, this arrangement minimizes the size of the distal end of the stylet 200 as well as minimizes the cost of production.

Another aspect of the present invention is the packaging of the ET 100 and stylet 200 as a pre-connected kit for immediate use. This packaging is particularly useful for emergency responders where seconds are critical to successful treatment. By having the stylet 200 and ET 100 packaged together with the stylet 200 pre-inserted into the ET 100 at the correct distance, the emergency responder need only open a single sterilized package and insert the ET 100 immediately. At the responder's choice the ET can be inserted before or after connection of the stylet 200 to the hand held camera device 300.

The stylet 200 can also be packaged and sold separately. This may be useful, particularly for emergency rooms and the like who receive patients or hold patients who have already been intubated, but the process of moving the patient may have caused the ET to shift, requiring review of its placement using the stylet 200.

While the present invention has been described at some length and with some particularity with respect to the described embodiments, it is not intended that it should be limited to any such particulars or embodiments or any particular embodiment, but it is to be construed so as to provide the broadest possible interpretation in view of the prior art and, therefore, to effectively encompass the intended scope of the invention.

We claim:

1. A device for insertion in a patient's body, the device comprising:
   a hand held display unit, said display unit including a trigger for actuating a camera;
   a stylet connectable to the display unit, the stylet being disposable, said stylet including a camera element formed at a distal end operable by the hand held display unit, and a light emitting element;
   a single use interconnect preventing the stylet from being reinserted into the hand held display unit once removed following an initial use, and
   a release disposed on the hand held display unit, the release for releasing the single use interconnect;
   wherein the single use interconnect is a mechanical stop formed at a proximal end of the stylet; and
   wherein the single use interconnect includes a stop that is released from inside the interconnect of the stylet, such that the released stop projects from interconnect outward and prevents reinsertion upon removal of the stylet from the hand held display unit.

2. The device of claim 1, wherein the stylet includes a camera element electrically connected to the hand held display unit.

3. The device of claim 1, wherein the camera element is a complimentary metal oxide semiconductor (CMOS) formed at a distal end of the stylet.

4. The device of claim 2, wherein a CMOS is connected to a printed circuit board (PCB).

5. The device of claim 4, wherein the PCB is T-shaped.

6. The device of claim 1, wherein the light emitting element is an LED positioned in a distal end of the stylet.

7. The device of claim 1, wherein the hand held display unit includes a display for showing pictures taken by the camera element.

8. The device of claim 1, wherein the hand held display unit includes a trigger for actuating the camera element.

9. The device of claim 1, wherein the hand held display unit includes a 30-second timer for optimizing the timing for insertion of an endotracheal tube into a patient.

10. The device of claim 1, further comprising a computer readable recording media and means for reading from the recording media, said computer readable recording media storing photographs taken by said camera element.

11. The device of claim 9, further comprising a mode or video button to switch the hand held display unit from a shoot mode to a display mode.

12. The device of claim 9, further comprising a next and a back button to view next and previous photographs taken by the camera element.

13. The device of claim 1, further comprising a length stop element.

14. The device of claim 13 wherein the length stop element limits a depth to which the stylet can be inserted into an endotracheal tube, and can be inserted into a port on the endotracheal tube.

15. The device of claim 13, wherein the length stop element is adjustable.

16. The device of claim 1, wherein the stylet includes markings along a length of the stylet that correspond to standard lengths for endotracheal tubes.

17. The device of claim 1, wherein a display portion of the hand held display unit is angled in a first direction with respect to a handle portion.

18. The device of claim 17, wherein a display portion of the hand held display unit is angled in a second direction with respect to a handle portion.

19. The device of claim 17, wherein a display portion of the hand held display unit and a handle portion are oriented at substantially 110 degree angle to each other, such that a display is tilted towards the user substantially 20 degrees.

20. The device of claim 19, wherein the a display portion of the hand held display unit is angled to either a left or right side at substantially a 20 degree angle to promote better view by a user.

21. The device of claim 1, wherein the camera element enables video clips to be made of an intubation procedure.

22. The device of claim 1, wherein a power source is in the hand held display unit.

23. A kit for intubation of a patient comprising:
an endotracheal tube;
a stylet for connection to a hand held display unit, the stylet being disposable, said stylet including a camera element formed at a distal end operable by the hand held display unit, and a light emitting element;
a single use interconnect preventing the stylet from being reinserted into the hand held display unit once removed following an initial use; and
a release disposed on the hand held display unit, the release for releasing the single use interconnect;
wherein the single use interconnect is a mechanical stop formed at a proximal end of the stylet, and
wherein the single use interconnect includes a stop that is released from inside the interconnect of the stylet, such that the released stop projects from the interconnect outward and prevents reinsertion upon removal of the stylet from the hand held display unit.

24. The kit of claim 23, wherein the stylet is pre-inserted into the endotracheal tube.

25. A hand held internal body scope device comprising:
a hand held display unit;
a stylet connectable to the display unit, the stylet being disposable, said stylet including a camera element formed at a distal end operable by the hand held display unit;
a single use interconnect preventing the stylet from being reinserted into the hand held display unit once removed following an initial use; and
a release disposed on the hand held display unit, the release for releasing the single use interconnect;
wherein the single use interconnect is a mechanical stop formed at a proximal end of the stylet, and
wherein the single use interconnect includes a stop that is released from inside the interconnect of the stylet, such that the released stop projects from the interconnect outward and prevents reinsertion upon removal of the stylet from the hand held display unit.

26. The hand held internal body scope device of claim 25, further comprising a light emitting element, for providing illumination for the camera element.

27. The hand held internal body scope device of claim 25, further comprising a trigger for actuating the camera element.

28. The hand held internal body scope device of claim 25, further comprising an insertion stop which engages an opening in an intubation tube, and integrates the intubation tube and a scope such scope enabling simultaneous manipulation of the intubation tube and the scope.

29. A hand held internal body scope device comprising:
a hand held display unit;
a stylet connectable to the display unit, the stylet being disposable, said stylet including a camera element formed at a distal end operable by the hand held display unit;
a single use interconnect preventing the stylet from being reinserted into the hand held display unit once removed following an initial use; and
a release disposed on the hand held display unit, the release for releasing the single use interconnect;
wherein the single use interconnect is an electronic stop preventing reuse of the stylet;
wherein the electronic stop prevents operation of the camera element when a previously used stylet is inserted into a scope;
wherein the scope records an identifier stored in the stylet, and prevents operation of the camera element when a stylet having a previously recorded identifier is inserted; and
wherein the scope assigns an identifier to the stylet upon initial insertion, records the assigned identifier, and prevents operation of the camera element when a stylet having an assigned identifier is inserted.

* * * * *